(12) United States Patent
McAlister

(10) Patent No.: US 8,840,692 B2
(45) Date of Patent: *Sep. 23, 2014

(54) ENERGY AND/OR MATERIAL TRANSPORT INCLUDING PHASE CHANGE

(75) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/584,795

(22) Filed: Aug. 13, 2012

(65) Prior Publication Data
US 2013/0206237 A1 Aug. 15, 2013

Related U.S. Application Data

(60) Provisional application No. 61/523,262, filed on Aug. 12, 2011.

(51) Int. Cl.
| | | |
|---|---|---|
| C01B 3/36 | (2006.01) |
| C01B 6/24 | (2006.01) |
| C01B 3/02 | (2006.01) |
| C10L 3/00 | (2006.01) |
| C07C 2/00 | (2006.01) |
| C10G 3/00 | (2006.01) |
| F17D 3/01 | (2006.01) |
| C10G 2/00 | (2006.01) |
| C07C 31/04 | (2006.01) |

(52) U.S. Cl.
CPC ... *F17D 3/01* (2013.01); *C10L 3/00* (2013.01); *C07C 2/00* (2013.01); *C10G 3/00* (2013.01); *C10G 2/00* (2013.01); *C07C 31/04* (2013.01)
USPC ............... 48/197 R; 423/644; 423/648.1

(58) Field of Classification Search
USPC ................................................. 48/197 R
See application file for complete search history.

(56) References Cited

U.S. PATENT DOCUMENTS 3,950,369 A * 4/1976 Gent ........................ 518/705
4,367,206 A 1/1983 Pinto
(Continued)

FOREIGN PATENT DOCUMENTS

CN 1918068 A 2/2007
CN 101448979 A 6/2009
(Continued)

OTHER PUBLICATIONS

International Search Report and Written Opinion for Application No. PCT/US2012/050670 Applicant: McAlister Technologies, LLC; Date of Mailing Feb. 26, 2013 (14 pages).

(Continued)

*Primary Examiner* — Matthew Merkling
(74) *Attorney, Agent, or Firm* — Perkins Coie LLP

(57) ABSTRACT

Techniques, systems and material are disclosed for transport of energy and/or materials. In one aspect a method includes generating gaseous fuel (e.g., from biomass dissociation) at a first location of a low elevation. The gaseous fuel can be self transported in a pipeline to a second location at a higher elevation than the first location by traveling from the first location to the second location without adding energy of pressure. A liquid fuel can be generated at the second location of higher elevation by reacting the gaseous fuel with at least one of a carbon donor, a nitrogen donor, and an oxygen donor harvested from industrial waste. The liquid fuel can be delivered to a third location of a lower elevation than the second location while providing pressure or kinetic energy.

29 Claims, 14 Drawing Sheets

(56) References Cited

U.S. PATENT DOCUMENTS

| | | | |
|---|---|---|---|
| 4,424,118 | A | 1/1984 | Rankel |
| 4,906,302 | A | 3/1990 | Bruya |
| 5,059,303 | A | 10/1991 | Taylor et al. |
| 5,630,528 | A | 5/1997 | Nanaji |
| 6,180,396 | B1 | 1/2001 | Ono et al. |
| 6,531,630 | B2 | 3/2003 | Vidalin |
| 6,673,742 | B2 | 1/2004 | Abdo et al. |
| 6,745,801 | B1 | 6/2004 | Cohen et al. |
| 6,875,794 | B2 | 4/2005 | Seiki et al. |
| 6,894,080 | B2 | 5/2005 | Seiki et al. |
| 6,984,305 | B2 | 1/2006 | McAlister |
| 7,082,969 | B1 | 8/2006 | Hollerback |
| 7,284,575 | B2 | 10/2007 | Gram et al. |
| 7,602,143 | B2 | 10/2009 | Capizzo |
| 7,608,439 | B2 | 10/2009 | Offerman et al. |
| 7,913,664 | B2 | 3/2011 | Williams et al. |
| 7,989,507 | B2 | 8/2011 | Rising |
| 8,070,835 | B2 | 12/2011 | McAlister |
| 8,215,342 | B2 | 7/2012 | McLean et al. |
| 8,352,071 | B2 | 1/2013 | Winsness |
| 8,485,233 | B2 | 7/2013 | Allinson et al. |
| 2003/0196810 | A1 | 10/2003 | Vinegar et al. |
| 2004/0204503 | A1 | 10/2004 | Beyer |
| 2005/0055874 | A1 | 3/2005 | Bekemeyer |
| 2007/0137246 | A1 | 6/2007 | McKellar et al. |
| 2008/0243310 | A1 | 10/2008 | Esposito et al. |
| 2009/0286890 | A1 | 11/2009 | Joshi et al. |
| 2009/0289227 | A1* | 11/2009 | Rising .......................... 252/373 |
| 2009/0318572 | A1 | 12/2009 | Sakai |
| 2011/0061376 | A1 | 3/2011 | McAlister |
| 2011/0061383 | A1 | 3/2011 | McAlister |
| 2011/0203669 | A1 | 8/2011 | McAlister |
| 2011/0288738 | A1 | 11/2011 | Donnelly et al. |
| 2011/0291425 | A1 | 12/2011 | Juranitch |
| 2012/0149786 | A1 | 6/2012 | McAlister |
| 2012/0167456 | A1 | 7/2012 | McAlister |
| 2012/0205004 | A1 | 8/2012 | Webb |
| 2013/0036670 | A1 | 2/2013 | McAlister |
| 2013/0112313 | A1 | 5/2013 | Donnelly et al. |

FOREIGN PATENT DOCUMENTS

| | | | |
|---|---|---|---|
| DE | 3933285 | A1 | 4/1991 |
| EP | 1002767 | A2 | 5/2000 |
| EP | 1219585 | A2 | 7/2002 |
| FR | 2897066 | A1 | 8/2007 |
| GB | 2086416 | | 5/1982 |
| JP | 2000-140621 | | 5/2000 |
| JP | 2002-193858 | | 7/2002 |
| JP | 2003-510403 | | 3/2003 |
| JP | 2005-075925 | | 3/2005 |
| JP | 2005-289856 | | 10/2005 |
| JP | 2008-537956 | | 10/2008 |
| JP | 2009-242248 | | 10/2009 |
| WO | WO 2004-092055 | | 10/2004 |
| WO | WO-2005021474 | A1 | 3/2005 |
| WO | WO 2005-033250 | | 4/2005 |
| WO | WO2010078035 | A2 | 7/2010 |

OTHER PUBLICATIONS

Dolan, Eric "Device uses sunlight to make liquid fuel". *The Raw Story*. Published: Dec. 24, 2010. 3 pages.

Lee et al., "Biological Hydrogen Production: Prospects and Challenges". *Trends in Biotechnology* 28.5. Jan. 2010. 10 pages.

Deluga et al., "AviationBioguels: Hydrotreated Renewable Jet," *General Electric*. Presentation Dated: Feb. 23, 2010. 13 pages.

International Search Report and Written Opinion for Application No. PCT/US2011/024799 Applicant: McAlister Technologies, LLC.; Date of Mailing: Oct. 18, 2011 (9 pages).

International Search Report and Written Opinion for Application No. PCT/US2011/24812 Applicant: McAlister Technologies, LLC.; Date of Mailing: Oct. 26, 2011 (12 pages).

Lopez et al., "Performance of the Southern California Edison Company Stirling Dish," Contractor Report, Prepared by Sandia National Laboratories Albuquerque, New Mexico, California, Printed Oct. 1993, 213 pages.

European Search Report for Application No. EP11742986.0 Applicant McAlister Technologies, LLC.; Date Mailed Feb. 17, 2014. 7 pages.

* cited by examiner

ENERGY AND/OR MATERIAL TRANSPORT INCLUDING PHASE CHANGE

CROSS-REFERENCE TO RELATED APPLICATION(S)

This application claims the benefit of and priority to U.S. Provisional Application No. 61/523,262, filed Aug. 12, 2011, entitled, "ENERGY AND/OR MATERIAL TRANSPORT INCLUDING PHASE CHANGE," which is incorporated herein by reference in its entirety.

BACKGROUND

This application relates to devices, techniques, and materials for forming, storing, reacting and transporting fuels and other materials.

Gaseous substances such as oxygen, nitrogen, carbon dioxide and fuels such as hydrogen and methane are more difficult and costly to store and transport than denser liquids or solids. For example, pressurizing hydrogen and/or methane can require sizeable capital expenditures, large energy expenditures for compression and/or to produce cryogenic liquids and attendant production of greenhouse gases, and high operating costs. Further, the pressure boosting equipment for transporting the pressurized hydrogen and/or methane through pipelines often incur costly maintenance, and repair costs.

In addition to the compressed-gas fuel form, hydrogen can be converted to cryogenic liquid or slush for storage. Liquid hydrogen is generally stored at −252° C. (−423° F.) at atmospheric pressure and, often transported through under insulated delivery lines, parts of which can be damaged due to atmospheric water vapor condensation and freezing. Storage and transport of cryogenic methane faces similar costs.

Moreover, the high cost of storage and transport for hydrogen and methane is met with low energy density. For example, a gallon of cryogenic liquid methane at −162° C. (−280° F.) provides an energy density of 89,000 BTU/gal, about 28% less than a gallon of gasoline. Liquid hydrogen at −252° C. provides only about 29,700 BTU/gal, about 76% less than gasoline.

BRIEF DESCRIPTION OF THE DRAWINGS

Like reference symbols and designations in the various drawings indicate like elements.

DETAILED DESCRIPTION

Overview

Figure 1A:
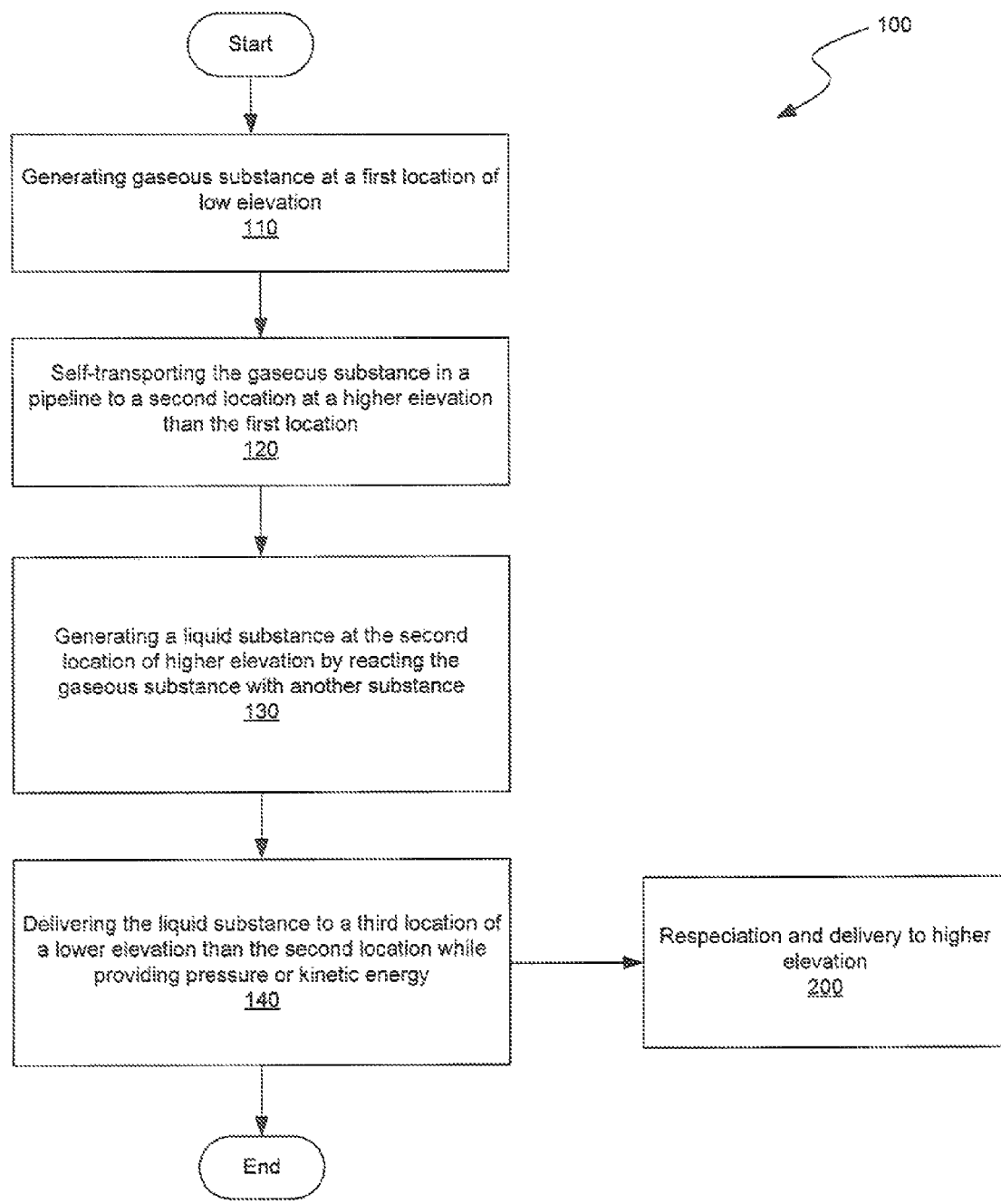
FIGS. 1A-1D are a process flow diagram of exemplary processes for generating fuel at one location and selectively respeciating the generated fuel or substance for storage and/or transport to another location.

In one aspect, a method of transporting energy and/or material can include providing or generating gaseous fuel (e.g., hydrogen gas from reforming methane produced by biomass dissociation) at a first location of a low elevation. The gaseous fuel can be self-transported in a pipeline to a second location at a higher elevation than the first location. For example, the gaseous fuel can travel from the first location to the second location without adding energy and the pressure at the higher elevation may be about the same pressure as the low elevation depending upon the flow rate and impedance of the pipeline. A liquid fuel or substance can be generated at the second location by reacting the gaseous fuel with at least one of a carbon donor (e.g., $CO_2$), a nitrogen donor (e.g., $N_2$), and an oxygen donor (e.g., $H_2O$). The carbon donor, nitrogen donor and/or oxygen donor can be harvested from industrial waste or the atmosphere. The liquid fuel or substance then can be delivered to a third location of a lower elevation than the second location while providing pressure or kinetic energy to accomplish useful work.

Implementations can optionally include one or more of the following features. Generating the gaseous fuel can include applying waste heat recovered from an external energy source or heat generated from a renewable energy source. The liquid fuel or substance can include at east one of a fuel oxygenate (e.g., methanol or ethanol), a liquid substance containing carbon and/or hydrogen, and a nitrogenous compound (e.g. ammonia). The method can include dissolving a hazardous contaminant into the liquid fuel to isolate the hazardous contaminant from an environment. The method can include applying heat to the liquid fuel to generate a gaseous fuel. The method can include transporting the gaseous fuel generated by applying heat to the liquid fuel to a fourth location at a higher elevation than the third location, for example, without adding energy or pressure.

In another aspect, a system for transporting fuel (e.g., renewable fuel) can include, a source (e.g., a biomass conversion plant) at a first location of a low elevation to provide or generate gaseous fuel (e.g., from biomass dissociation). Methane (e.g., from the biomass dissociation) can be dissociated or reformed to release hydrogen gas. A first pipeline can connect the source and deliver such hydrogen to a second location of higher elevation than the first location. The system can be configured and operated such that the gaseous fuel can continuously or intermittently be added at the first location, fill the space provided within the pipeline, and thus travel from the first location to the second location, for example, without added energy or pressure. The system also can include a reactor at the second location configured and operated to generate a liquid fuel or substance such as a fuel alcohol or an alkane (e.g. paraffinic ethane, propane, butane, etc.) or a nitrogenous substance (e.g. ammonia) or various other compounds that are dissolved or held in solution by selected solvents (e.g. urea $CH_4N_2O$, guanidine $CH_5N_3$, etc.). The reactor can be configured, for example, to react the gaseous fuel with at least one of a carbon donor, a nitrogen donor, and an oxygen donor. A second pipeline can connect the reactor to a third location of a lower elevation than the second location. The system can be configured such that energy from flow of the liquid fuel generated at the second location is collected to perform useful work at the third location or between the second location and the third location.

In another aspect, transporting fluid substances through pipelines across terrain that is relatively flat also benefits from controlled phase changes including process reactions. Illustratively each of the eight sites in the embodiments shown herein could be at the same or lower elevations and the forces needed to provide for the same deliveries and operations can be achieved by generating sufficient gas pressure that can be applied to the liquid phases to provide the deliveries indicated. Illustratively a portion of the chlorine at gas pressure provided by electrolysis of fused or dissolved halite can be sufficient to deliver liquid hydrogen chloride or hydrochloric acid. A traveling separator or "pig" that seals the pressurized gas from the liquid improves the efficiency and prevents for example, intermingling of chlorine with hydrogen chloride. Upon delivery of the hydrogen chloride and the separating pig to a predetermined site, the expanded chlorine can then be reacted with hydrogen to produce, additional hydrogen chloride that can be included in the inventory of hydrogen chloride that is delivered to the predetermined site.

Implementations can optionally include one or more of the following features. The reactor can include a heat exchanger (e.g., a countercurrent heat exchanger) to apply waste heat recovered from an external energy source or heat generated from a renewable energy source. The system can include a contaminant recovery system operably connected to the reactor. The contaminant recovery system can be configured to harvest a hazardous contaminant and mix the harvested hazardous contaminant into the liquid fuel to isolate the hazardous contaminant from an environment. The system can include a second reactor at the third location configured to dissociate the liquid fuel or substance (e.g., using an anaerobic reformation or dissociation reaction) to generate a gaseous fuel or substance. The system can include a second heat exchanger (e.g., a countercurrent heat exchanger) operably connected to the second reactor to apply heat to the liquid fuel to generate the gaseous fuel. The system can include a third pipeline connecting the second reactor to a fourth location of a higher elevation than the third location The third pipeline can be configured such that the gaseous fuel moves to the fourth location without adding energy or pressure.

The subject matter described in this specification potentially can provide one or more of the following advantages. For example, the described techniques and systems can be used to avoid the high costs of compressing or cryogenically freezing fuels, such as hydrogen and methane fuels. In addition, the costs associated with maintaining a pipeline for transporting liquefied hydrogen fuel can be avoided. The described techniques can be used to selectively respeciate a fuel for efficient storage and transport.

Energy and/or Material Transport System

Gaseous or vaporous substances fill a pipeline at a lower elevation and can thus provide delivery from a lower elevation to a higher elevation. And such gaseous or vaporous substances can perform work at the higher elevation by expanding from the delivery pressure of the pipeline to a lower application pressure at the higher elevation. Liquids or solutions of solids in liquids may be formed from such substances travel in a pipeline from the higher elevation to a lower elevation. And thus such liquids can produce pressure and/or kinetic energy to do work at the lower elevation. Throughout this disclosure, the singular terms "a," "an," and "the" include plural referents unless the context clearly indicates otherwise. Similarly, the word "or" is intended to include "and" unless the context clearly indicates otherwise.

The difficulty if not economic barrier to economical transportation and storage of hydrogen and other fluids is high due to the low density of hydrogen and other fluids to be densified as liquids or expanded as gases including such phase changes that may result from entering into various valuable compounds, dissociations, or respeciations. Several embodiments of the described techniques and systems take advantage of this fluid characteristic of gaseous property. As described herein, gaseous fuel (e.g., hydrogen and gaseous mixtures including hydrogen) can be provided or generated (e.g., from biomass waste at the source of the biomass waste) at a low elevation location and transported (e.g. self-delivered) to a higher elevation second location. Gaseous fuel can be any fuel or mixture including fuel that is a gas at standard temperature and pressure. Hydrogen is ordinarily a gaseous substance or fuel and can be reacted and/or respeciated to a solid or liquid fuel (e.g., urea, alcohol or ammonia) which can be delivered to a lower elevation third location as a part of an energy or substance delivery or divergence process. Such solutions, mixtures and liquids can be any substance or fuel or mixture including fuel that is a liquid at selected or induced transport temperature and pressure. The delivery to the lower elevation can provide pressure and/or kinetic energy and/or perform work at the lower elevation or between the higher elevation and the lower elevation.

FIG. 1A is a process flow diagram of an exemplary process 100 for generating a substance such as a fuel at one location and selectively respeciating the generated substance for storage and/or transport to another location. A system (e.g., system 400 shown in FIG. 4) can generate gaseous fuel (e.g., hydrogen or a gaseous compound or mixture including hydrogen) from biomass digestion, dissociation or another process at a first location of a low elevation (110). Self expanding and transporting substances and/or fuels and/or gases and/or vapors may be transported at selected or induced transport temperatures and pressures. Exemplary processes to generate hydrogen are described in U.S. application Ser. No. 13/027,068, filed on Feb. 14, 2011 and incorporated herein by reference in its entirety. Biomass digestion and/or dissociation to generate hydrogen is further described with respect to FIGS. 5 and 6. In place of gaseous fuels derived from biomass, embodiments of the present technology can be used with other gaseous materials, such as gaseous materials generated by alternative processes. For example, hydrogen gas from steam reforming natural gas derived from sources other than biomass (e.g., from geological deposits) or from electrolysis of a substance such as butyric and/or acetic acid and/or water can be used in place of the gaseous fuels derived from biomass described herein.

The gaseous substance can be self-transported from the low elevation location to a second location of a higher elevation (120). For example, the gaseous substance or fuel fills the space available and can freely rise to the higher elevation second location without any added energy or pressure. At the higher elevation second location, the freely transported gaseous substance can do work by conversion of kinetic and/or pressure energy and can be converted to a liquid substance or fuel. In certain embodiments, some portion of such transported substance or fuel may be heated by sources and/or methods such as combustion and/or an application of heat from a renewable resource such as solar, wind, moving water or geothermal energy. The liquid substance can be, for example an alcohol or ammonia (130). For example, at the second location of higher elevation, the gaseous fuel can be reacted with a reagent such as a carbon donor (e.g. CO or $CO_2$), a nitrogen donor (e.g., $N_2$) and an oxygen donor (e.g., air or $H_2O$) or a reagent harvested from industrial waste.

The generated substance or liquid fuel can be transported to a third location of a lower elevation (140) by a pipeline or another conveyance that "runs" downhill. Energy from head and/or flow of the liquid substance can be used to perform useful work at the third location or between the second location and the third location. For example, the liquid substance (e.g., methanol, ethanol, propanol, butanol, and/or various other compounds such as ammonia or urea) can have a head in a pipeline on delivery to the third location and/or turn a turbine as it descends to the third location. The substance and/or fuel delivery can do work and continue by respeciating the high density substance at the third location of low elevation to a gaseous substance and self-transporting the gaseous fuel constituents such as carbon monoxide, carbon dioxide, nitrogen, and hydrogen to a fourth location of a higher elevation.

FIG. 16 shows an exemplary embodiment that provides a system at a factory about 50 m (164') above sea level sea level including a first pressure electrolyzer that utilizes a combination of converted wind, solar and wave energy to electrolyze and dissociate a halogen salt such as sea-salt halite or NaCl into sodium and chlorine (i.e. $NaCl \rightarrow Na+Cl$). At this first coastal site the elevated pressure of the electrolyzer is 200 Bar and the chlorine gas fills a pipeline from the first low elevation electolyzer site to pressurize a pipeline that delivers to a factory that is at an elevation of 1600 m (5250') above sea level and 75 miles inland. The first low elevation electrolyzer site continues to add chlorine at the rate that it is taken from the higher elevation second site location. The pipeline operates as a significant energy and chlorine storage and delivery system. Recovery of much of the work by the first electrolyzer is accomplished by depressurizing chlorine through a turbo-generator and as it enters a reactor at the second higher elevation site that produces hydrogen chloride ($H_2+2Cl \rightarrow 2HCl$) using hydrogen produced by solar heated dissociation of forest slash to produce carbon and hydrogen. Hydrogen chloride or a suitable acid that is formed with water at the second elevated site is delivered through another pipeline to a third lower elevation site at 400 m (1312') about 200 miles further inland where the hydrogen chloride or hydrochloric acid liquid does work by conversion of kinetic energy and/or the pressure energy representing the altitude difference from the second higher elevation at 1600 m to the third elevation at 400 m. At the third elevation site a second electrolyzer produces pressurized hydrogen and chlorine at a suitable pressure such as 200 Bar. A 200 Bar pipeline delivers hydrogen and another 200 Bar pipeline delivers chlorine from the third elevation site to a fourth site at a 1800 m (5905') elevation about 50 miles further inland. The fourth elevation site receives work by depressurizing hydrogen and chlorine through turbo-generators and these reactants are entered into separate reactors. One reactor produces calcium chloride for use in a local vegetable cannery and the other produces wet methanol ($3H_2 + CO_2 \rightarrow CH_3OH+H_2O$) a liquid that is delivered to a fifth site at 900 m (3000') about 300 miles further inland where it is converted to a higher energy density fuel by additions of colloidal and/or soluble carbon donor from wastes such as tainted food and medications. Heat ($\Delta$) such as solar or geothermal heat drives the reaction ($\Delta CH_3OH+H_2O+C \rightarrow 3H_2+2CO$) to convert the liquid solution to self-pressurized gaseous carbon monoxide and hydrogen. Another pipeline from the fifth site to a higher elevation sixth site at 1500 m (4920') about 100 miles further inland gains work by a turbo-generator that depressurizes the mixture of hydrogen and carbon monoxide that is subsequently utilized to remove nickel from spent catalyst substrates and other scrap to form gaseous $Ni(CO)_4$. This nickel carbonyl is and transported as a warm mixture with hydrogen in an insulated and/or heat generating subsystem and pipeline for delivery to a seventh site at 1830 m (6000') about 50 miles further inland, where the nickel carbonyl and hydrogen is expanded to do work and upon cooling the nickel carbonyl forms a liquid that separates from the hydrogen. The hydrogen is reacted with a carbon donor such as forest slash, farm or municipal solid wastes to produce condensable products such as ethane or ethylene and/or propane or propylene and such condensed liquids are delivered by one or more pipelines to station eight at a 1000 m (3280') altitude where work is accomplished by pressure and/or kinetic energy conversion. The separated liquid carbonyl is delivered by a pipeline to a lower elevation site for producing nickel products at 800 m (2800') about 100 miles further inland where work is done by the pressure and/or kinetic energy that the drop in altitude provides. Dissociation of the nickel carbonyl ($Ni(CO)_4 + \Delta Ni + 4CO$) provides nickel along with carbon monoxide for reacting with locally produced hydrogen from a source such as dissociation of methane from an anaerobic digester. Liquid methanol ($CO+2H_2 \rightarrow CH_3OH$) thus produced can be delivered by a pipeline to another lower location or used locally to, fuel engines.

Figure 1B:
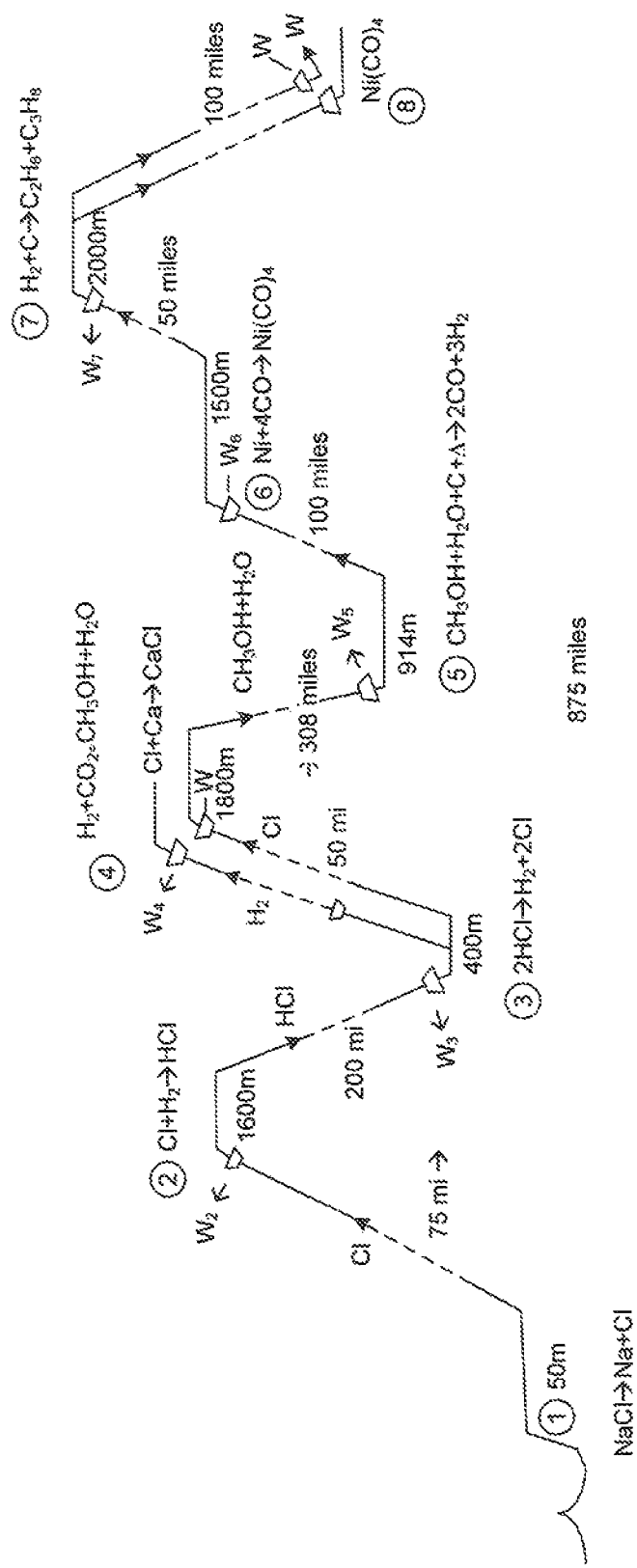
Figure 1C:
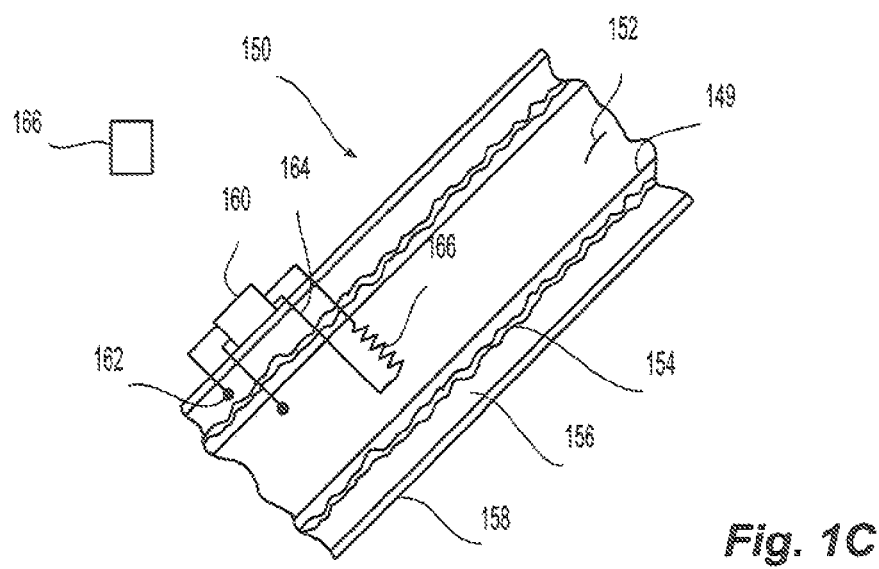
Figure 1D:
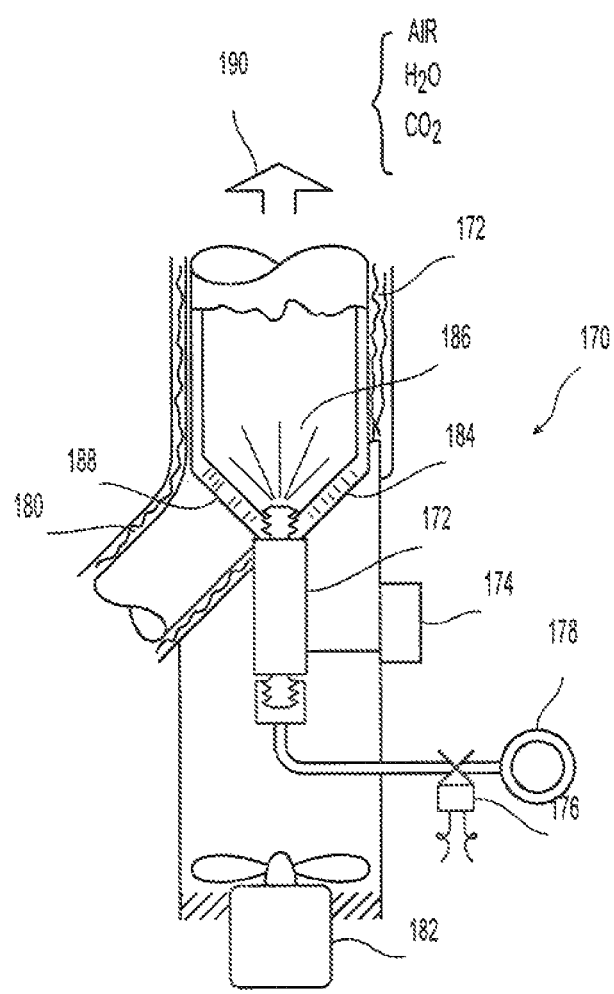

FIG. 1C shows the cross section of a pipeline embodiment 150 for safely transporting a hazardous fluids such as metal carbonyls. Iron and nickel carbonyls, which are poisonous substances can be transported as a liquid at one temperature and upon heating become gaseous. Illustratively nickel carbonyl ($Ni(CO)_4$) is liquid below about 42.2° C. (108° F.) and is gaseous at higher temperatures, having a critical temperature of 193° C. (380° F.). Passageway 152 provides smooth flow for gaseous nickel carbonyl, which is maintained at temperatures above 43.3° C. (110° F.) by maintenance of its starting temperature with one or more internal heaters 166 and/or layers of insulation 154 including a controlled pressure of an insulating gas such as argon or sulfur hexafluoride that is contained in the annular space between outer pipe 158 and inner pipe 148 at a pressure exceeding the pressure within channel 152. Probes 162 and 164 continuously monitor the chemical, thermal, and physical conditions of the insulating gas and the nickel carbonyl flowing through conduit 152 and microprocessor 160 provides temperature control and trend analysis of chemical identifications and physical conditions in conduit 152 and gaseous insulating space 156. Conduit 149 is maintained isolated from potential corrosion and safe from tensile forces by compressive forces exerted by pressurized insulating and isolating gas contained in space 156. As shown in FIG. 1D, information from 160 is provided to system controller 166 by wire, wireless radio frequency, optical, or other methods to enable the contents of passageway to be quickly delivered, to a burner 170 for fail-safe combustion ($Ni(CO)_4+2O_2 \rightarrow Ni+4CO_2+\Delta$) if an incipient containment failure of conduit 149 is indicated. Upon such fail-safe occasions the contents of conduit 149 are emptied into conduit 180 through louvers 188 (shown in FIG. 10) in one or more strategically placed burners 170 and conduit 149 is purged with hot air from an air heater application of burner 170 while maintaining an oxidizing combustion in other emergency burners 170 with a fuel such as hydrogen which is maintained at pressure in line 178 (shown in FIG. 10).

Figure 10:
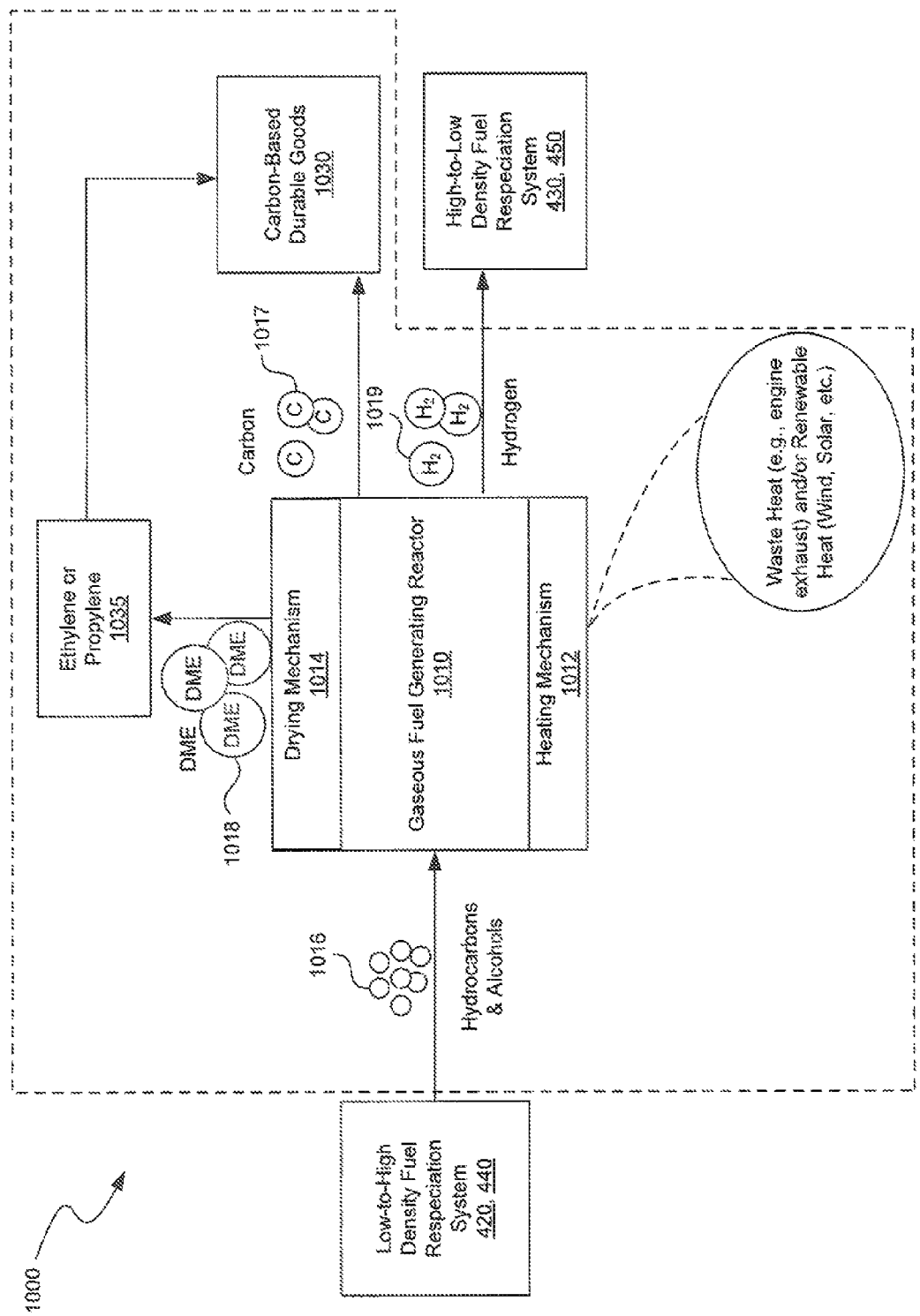
FIG. 10 is a block diagram of a system for respeciating liquid fuel to generate gaseous fuel.

FIG. 10 shows in operation air delivery by fan 182 and/or the draft produced by pressurized delivery by combined fuel injection of hydrogen and plasma ignition that may be separately provided or combined by a device that integrates fuel delivery and ignition functions. Hydrogen provided through solenoid valve 176 for continuous combustion 186 provides assured combustion of nickel carbonyl in surplus air that is drawn into the combustion zone 186 and/or forced by fan 182 through louvers 184. This assures that the gases exiting emergency burner 170 are surplus hot air along with water vapor and carbon dioxide until all traces of nickel carbonyl are purged from conduit 149.

Transporting fluid substances through pipelines across terrain that is relatively flat also benefits from controlled phase changes including process reactions illustratively each of the eight sites in the embodiments of FIG. 1B could be at the same or lower altitudes and the forces needed to provide for the same deliveries and operations can be achieved by generating sufficient gas pressure that can be applied to the liquid phases to provide the deliveries indicated. Illustratively a portion of the chlorine at gas pressure provided by electrolysis of fused or dissolved halite can be sufficient to deliver liquid hydrogen chloride or hydrochloric acid. A traveling separator or "pig" that seals the pressurized gas from the liquid improves the efficiency and prevents for example, intermingling of chlorine with hydrogen chloride. Upon delivery of the hydrogen chloride and the separating pig to site 3 the expanded chlorine can be reacted with hydrogen to produce additional hydrogen chloride that can be included in the inventory of hydrogen chloride delivered to site 3.

Figure 2:
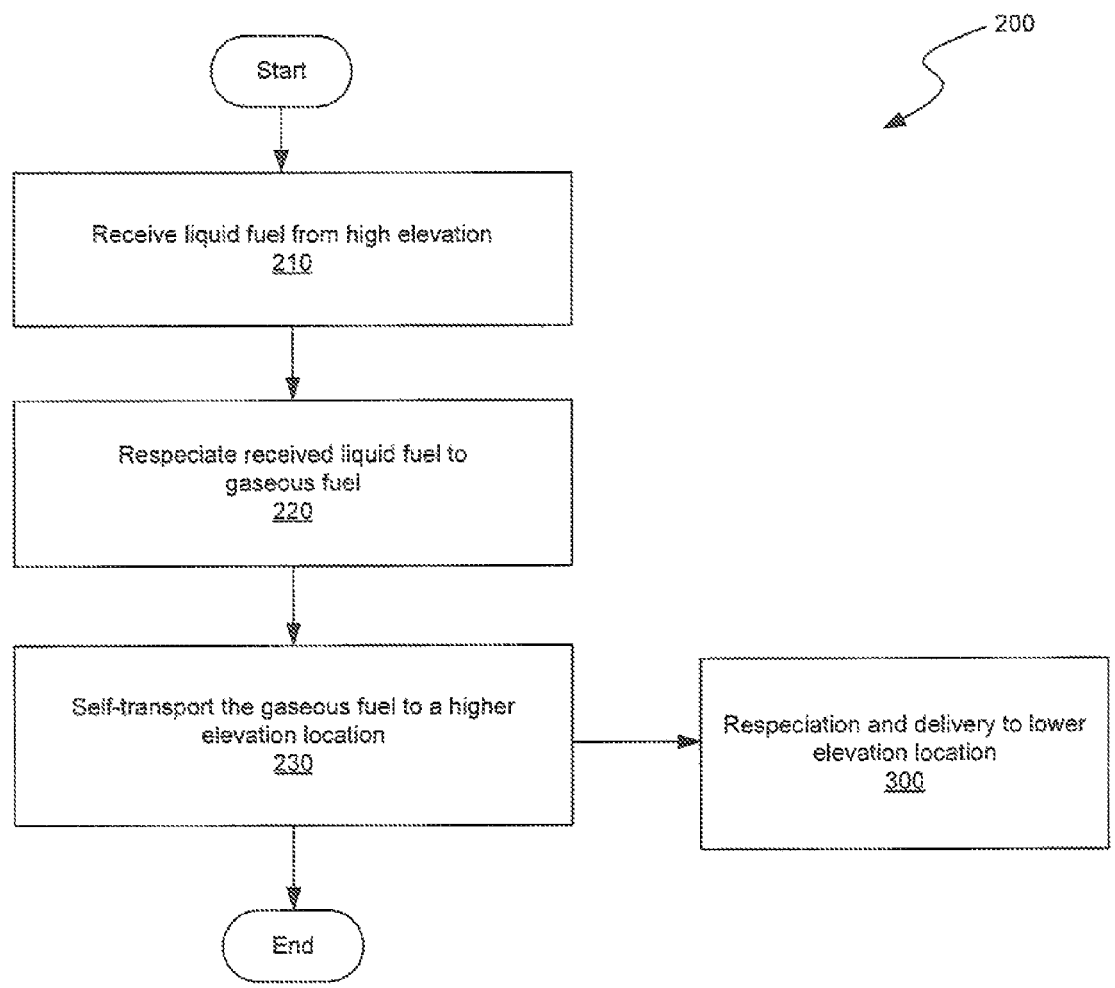
FIG. 2 is a process flow diagram of an exemplary process for respeciating liquid fuel or substance at a lower elevation to gaseous fuel and delivering the gaseous substance to a higher elevation.

FIG. 2 is a process flow diagram of an exemplary process 200 for transferring a selected liquid mixture or substance from a higher elevation to a lower elevation, respeciating liquid fuel or mixture or substance at a lower elevation to one or more gaseous fuels or constituents and delivering the gaseous fuels or constituents to a higher elevation. A system (e.g., system 430 shown in FIG. 4) can receive the liquid fuel from the higher elevation location (210). The system can respeciate the liquid fuel or substance to obtain gaseous fuel or constituents (220). The gaseous substances, fuels and/or other constituents can be self-transported to a higher elevation location (230). The self-transported gaseous fuel can be respeciated and delivered as a gas, vapor, liquid or mixture to a lower elevation location again, as shown in the process 300 of FIG. 3 below.

Figure 3:
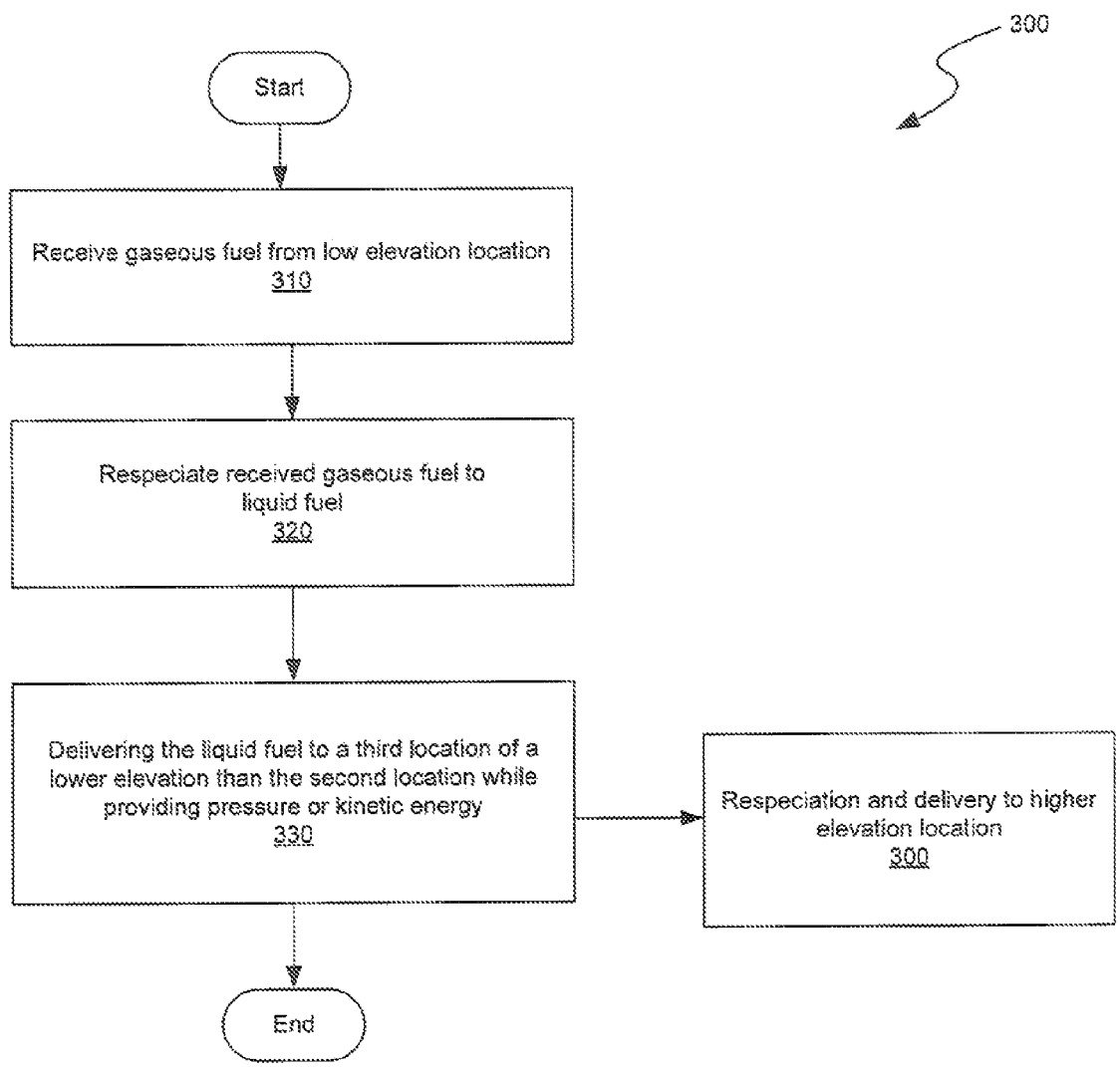
FIG. 3 is a process flow diagram of an exemplary process for respeciating gaseous fuel or substance at the higher elevation to obtain liquid fuel or substance and delivering the liquid fuel or substance to a lower elevation.

To continue transporting the fuel, the gaseous fuel received at the higher elevation location can be respeciated and delivered to a lower elevation location. FIG. 3 is a process flow diagram of an exemplary process 300 for respeciating gaseous or vaporous substances at the high elevation location to obtain a liquid fuel and delivering the liquid fuel to a lower elevation location. A system (e.g., system 440 shown in FIG. 4) receives the gaseous fuel from the lower elevation location (310). The system respeciates the received gaseous fuel to obtain liquid fuel (320). The liquid fuel then can be transported to a lower elevation location (330).

The selective respeciation and delivery of the fuel as shown and described in processes 200 and 300 are alternately performed until the fuel and/or selected constituents are delivered to any number of desired locations as may be induced and controlled by the temperature and/or pressure conditions that are selected and maintained in each stage of the overall process. Described below are processes and systems for respeciating and delivering various constituents and/or species of the fuel.

Figure 4:
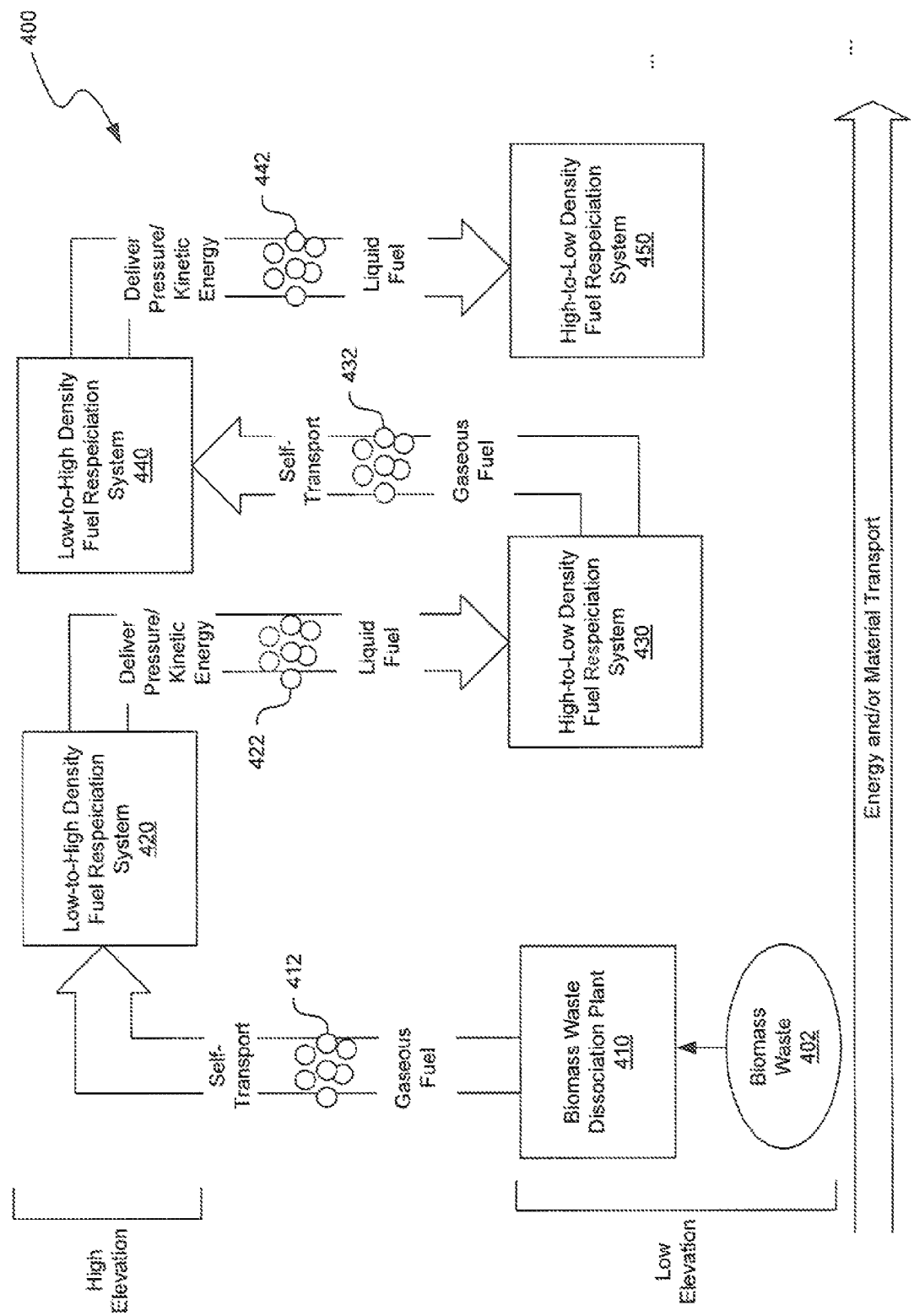
FIG. 4 is a block diagram of a system for generating renewable fuel from biomass waste, selectively respeciating the generated fuel and delivering the selectively respeciated fuel to a target location.

FIG. 4 is a block diagram of a system 400 for generating renewable fuel from biomass such as found in permafrost, methane hydrate forming sediments, sewage, garbage, forest slash and/or farm waste 402, selectively respeciating the generated fuel, and delivering the selectively respeciated fuel constituents to a target locations. The system 400 includes a biomass digestion and/or dissociation plant 410 at the source of the biomass waste 402, such as a burnt down forest. The biomass waste dissociation plant performs biomass dissociation to generate various species of fuel including hydrogen 412, as described in U.S. patent application Ser. No. 13/027,068, filed Feb. 14, 2011 (attached hereto as Appendix 1). Biomass dissociation to generate various chemical species is further described with respect to FIGS. 5 and 6 below.

The gaseous fuel (e.g., gaseous hydrogen) 412 is self-transported to a low-to-high density fuel respeciation system 420 at a higher elevation location. Examples of reactions for respeciating the gaseous fuel to obtain liquid fuel 422 are described further below.

The liquid fuel (e.g., an alcohol, or ammonia) 422 is delivered to a high-to-low density fuel respeciation system 430 at a lower elevation location. Examples of reactions for respeciating the liquid fuel to obtain gaseous fuel are described further below.

The system can include additional numbers of low-to-high density fuel respeciation systems and high-to-low density fuel respeciation systems as needed to deliver selected portions of the fuel to one or more desired target location. For example, the system 400 in FIG. 4 is shown in include a second low-to-high density fuel respeciation system 440 and a second high-to-low density fuel respeciation system 450 for illustrative purposes only.

In the example shown in FIG. 4, the high-to-low density fuel respeciation system 430 respeciates the liquid fuel to obtain gaseous fuel 432, which is self-transported to the second low-to-high density fuel respeciation system 440 at the higher elevation. The second low-to-high density fuel respeciation system 440 respeciates the gaseous fuel to obtain liquid fuel 442, which is delivered to the second high-to-low density fuel respeciation system 450. Additional energy conversion steps may include optional production of work by harnessing kinetic, pressure and/or chemical energy potentials a selected sites as shown in FIGS. 1A-1D and 3.

The system 400 can be implemented to transport fuel across both natural and manmade environments. For example, the high and low elevations can be high and low elevations of natural topography (e.g., peaks and valleys). Alternatively, the high and low elevations can be venous levels of manmade structures. For example, hydrogen can be produced at the base of a building and delivered to the top of the building. Energy conversion can be performed at the top of the building to respeciate the hydrogen to generate a denser substance such as a hydrogenous compound or water and deliver the generated water to the bottom of the building. Also, at the top of the building, the hydrogen can be converted into an alcohol or ammonia which can be delivered to a bottom of another building as an energy conversion step. The respeciation and transport processes can continue from one budding to another or from a valley to a peak and from the peak to another valley until the fuel is delivered to a target location.

The overall energy for the incidental constituent availability and environmental conditions along with manufacturing and transportation processes can be favorable due to the self-transportable nature of the gaseous fuel and the self-generated pressure and/or kinetic energy of the liquid fuel. Also, the carbon, nitrogen, oxygen, and/or hydrogen donors used in the respeciation processes can be harvested and recycled from industrial processes (e.g., $CO_2$ from fossil fuel exhausts).

Biomass Waste Dissociation

Figure 5:
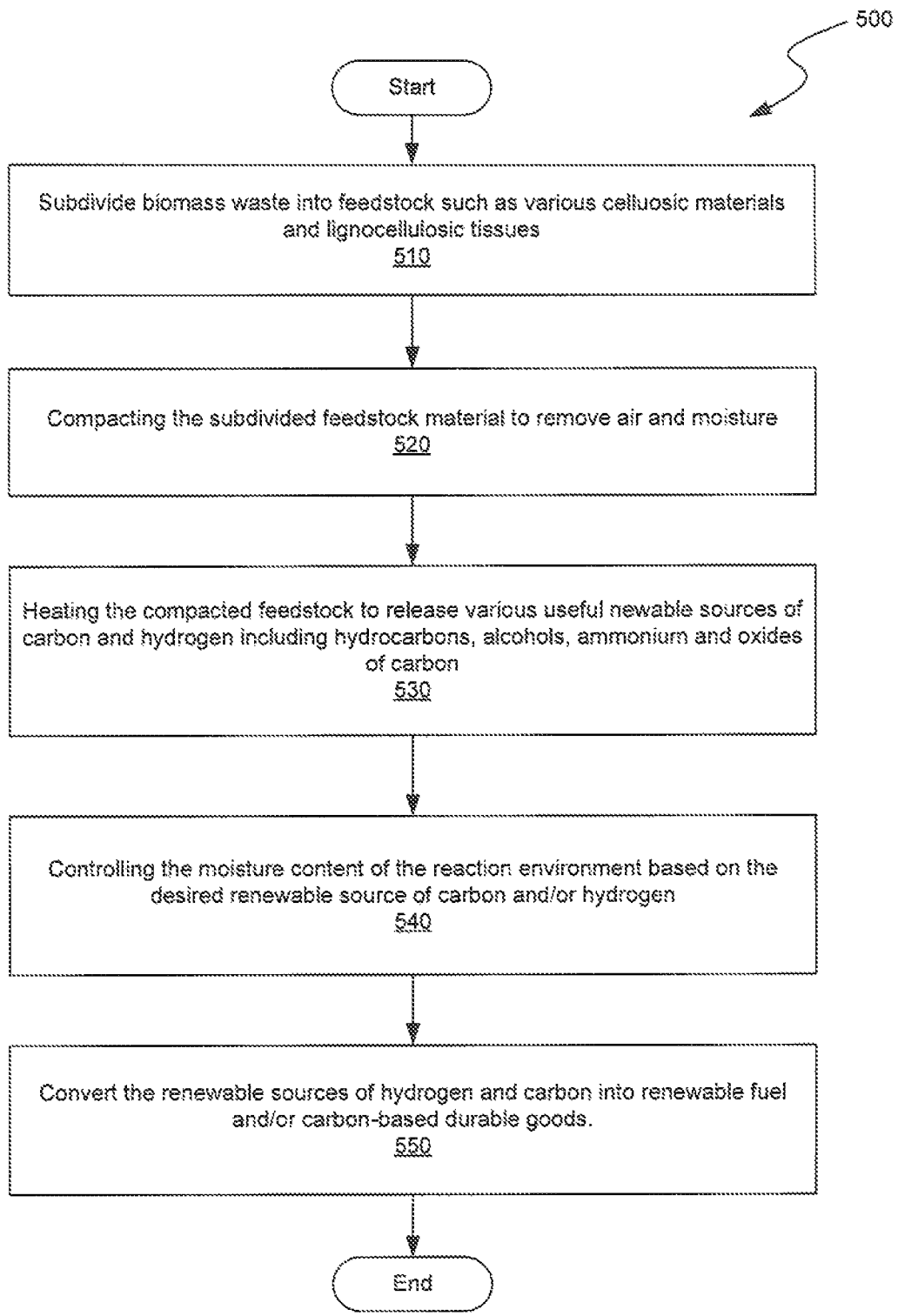
FIG. 5 shows a process flow diagram of a process for a rapid conversion of carbon, hydrogen, and oxygen containing biomass wastes into useful renewable sources of carbon and hydrogen that can be used to produce carbon-based durable goods and renewable fuel.

FIG. 5 shows a process flow diagram of a process 500 for a rapid conversion of carbon, hydrogen, and oxygen containing biomass wastes into useful renewable sources of carbon and hydrogen that can be used to produce carbon-based durable goods and renewable fuel. The process 500 is analogous to the process 110 in FIG. 1 above.

A system (e.g., a biomass dissociation system 600 below) can subdivide the biomass waste into feedstock materials such as various cellulosic materials and lignocellulosic tissues (510). The subdivided feedstock materials can be compacted to remove air and moisture (520). The compacted biomass waste feedstock can be heated to release various useful renewable sources of carbon and/or hydrogen, such as hydrocarbons, alcohols, ammonium, and oxides of carbon (530). Also, the moisture content of the overall reaction environment can be controlled based on the desired renewable source of carbon and/or hydrogen (540). To control the moisture content, the compacted biomass waste feedstock that has been completely dried and de-aired can be used as a desiccant, for example. The renewable sources of hydrogen and carbon can be used to generate renewable fuel and/or carbon-based durable goods (550).

For example, as shown in Equation 1, biomass wastes can be heated sufficiently in an anaerobic environment to release desirable gases, carbon, and solid residues, such as mineral oxides and other compounds. The anaerobic process for producing oxides of carbon, hydrogen, and/or hydrocarbons from biomass wastes summarized in Equation 1 is not balanced for any particular type, amount, or ratio of lignin, cellulose, or other biomass feedstock.

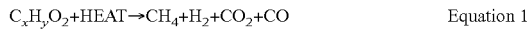

$$C_xH_yO_z + HEAT \rightarrow CH_4 + H_2 + CO_2 + CO \qquad \text{Equation 1}$$

Using the process described in Equation 1, virtually any organic material can be converted in large part to hydrocarbon fuel, such as methane ($CH_4$) for distribution and storage in the existing natural gas infrastructure. Equation 2 below illustrates a general summary of the overall reactions for production of methane from typical biomass wastes such as glucose, lignin, and cellulosic feedstocks.

$$C_6H_{12}O_6 + HEAT \rightarrow 3CH_4 + 3CO_2 \qquad \text{Equation 2}$$

In some implementations, the biomass dissociation reaction can produce alcohols, such as methanol as a readily storable and transportable liquid fuel and chemical precursor. Methanol or "wood alcohol" can be extracted by heating lignocellulosic wastes through partial combustion or by anaerobic heating processes. Equations 3 and 4 summarize the output of methanol that can be achieved by selection of different anaerobic operating temperatures, pressures and catalysts.

$$C_6H_{12}O_6 + HEAT \rightarrow 6CO + 6H_2 \qquad \text{Equation 3}$$

$$6CO + 6H_2 \rightarrow 3CH_3OH + 3CO \qquad \text{Equation 4}$$

At higher feed rates and/or lower heat release rates, in a reactor, the charge dells not reach the higher temperatures that produce the gases shown in Equation 1, and the dissociation process produces alcohol, such as methanol. Carbon monoxide can be separated from methanol by cooling the methanol vapors to form liquid methanol. The separated carbon monoxide can be used to fuel an engine, to release heat through combustion by a burner assembly, and/or to form hydrogen by a reaction with water as summarized in Equation 5. Hydrogen produced by the reaction summarized in Equation 5 can be used to produce methanol as shown in Equation 4, to improve operation of an engine, to improve the yield of methane and/or ethane in the biomass conversion, and/or as a heating fuel.

$$CO + H_2O \rightarrow H_2 + CO_2 \qquad \text{Equation 5}$$

Figure 6:
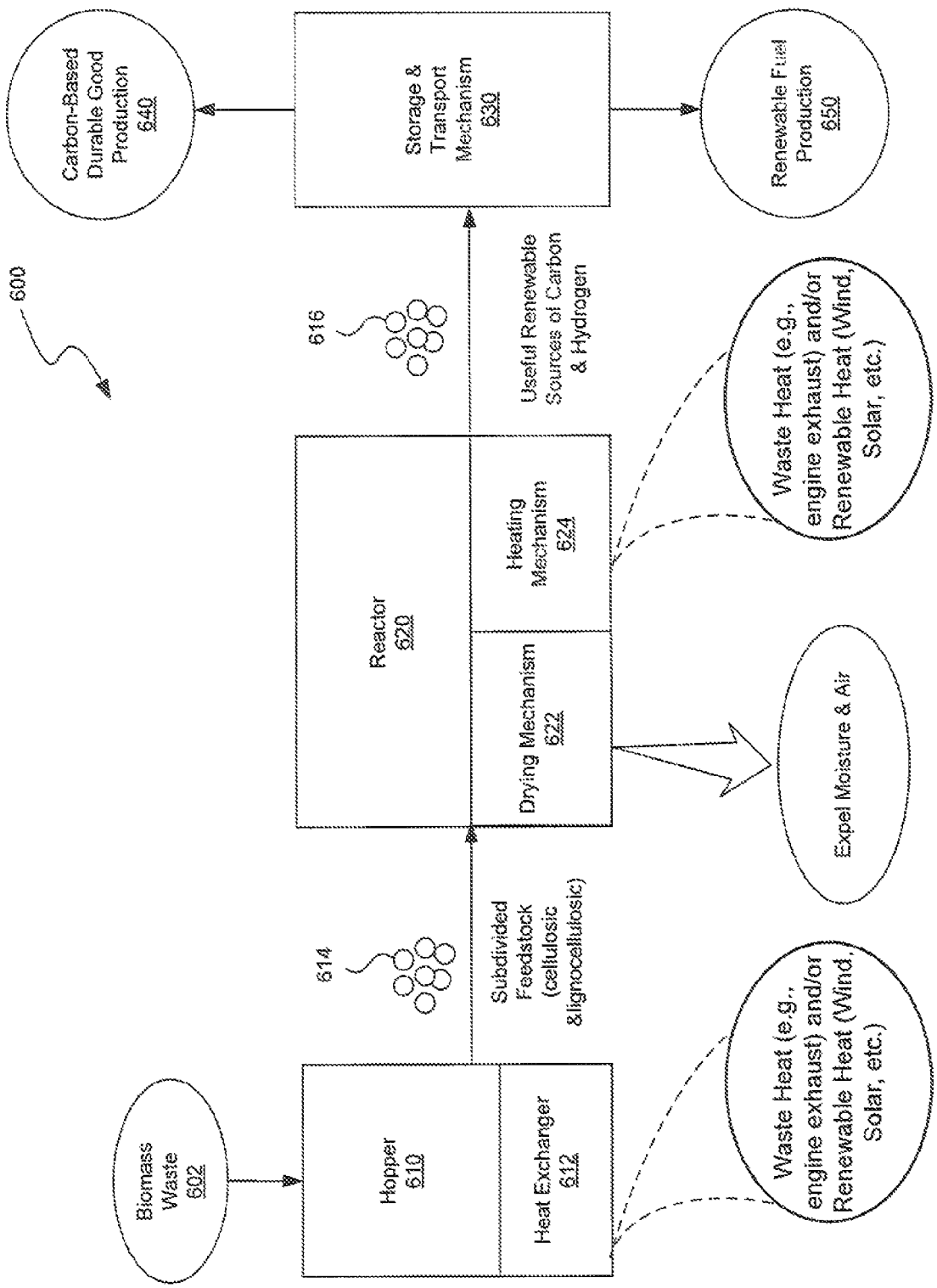
FIG. 6 shows an exemplary system for dissociating biomass waste into hydrogen and carbon carrying intermediaries.

FIG. 6 shows an exemplary system 600 for dissociating biomass waste 602. The system 600 is analogous to the system 410 in FIG. 4. The system 600 includes a biomass waste intake component, such as a hopper 610 that receives the biomass waste in raw form and breaks down (e.g., chips, chops, grinds, etc.) the raw material into subdivided feedstock 614, such as various cellulosic and lignocellulosic materials. The hopper 610 can include a heating mechanism, such as a heat exchanger 612 to pre-heat the subdivided feedstock. The heat exchanger can recapture and recycle waste heat from an external heat source (e.g., engine exhaust and/or renewable heat, such as wind, solar, etc.) or from the reactor 620.

The subdivided (and in some implementations, pre-heated) feedstock is forwarded to a reactor 620 to dissociate the biomass waste feedstock into useful renewable sources of carbon and hydrogen, such as various hydrocarbons, alcohols, ammonia, and oxides of carbon. The reactor 620 can include a drying mechanism 622 to expel moisture and air from the feedstock. The drying mechanism 622 can include an extruding device to physically "squeeze out" the moisture and air from the feedstock. Examples of the extruding device include a helical screw conveyer and a ram piston conveyer. Also, the drying mechanism 622 can include one or more heating mechanisms, such as heat exchangers that capture heat generated by the reactor 620 and recycle the captured heat to dry the feedstock. The heat exchangers can also recapture and recycle waste heat from an external heat source (e.g., engine exhaust and/or renewable heat, such as wind, solar, etc.).

The reactor 620 can also include a heating mechanism 624 for generating adequate heat used in an anaerobic reaction to dissociate the biomass waste feedstock into the useful renewable sources of carbon and hydrogen 616, such as hydrocarbons, alcohols, ammonia, and oxides of carbon. The generated useful renewable sources of carbon and hydrogen 616 can be forwarded to a storage and/or transport mechanism 630 to be used in additional reactions to generate renewable fuel and/or carbon-based durable goods in respective reaction systems 640 and 650 for either carbon-based durable good production or renewable fuel production. Moreover, the storage and/or transport mechanism 630 allows for efficient transport of the useful renewable sources of carbon and hydrogen 616 to remote locations for further processing.

The reactor 620 can be configured to increase the thermal efficiency of the biomass waste conversion process while reducing or eliminating carbon dioxide formation. For example, the reactor 620 can include mechanisms to perform countercurrent drying (e.g., recycling heat) and elimination of air, moisture, and other oxygen donors prior to extraction of carbon, hydrocarbons (e.g., methane), and/or hydrogen.

Respeciation of Gaseous Fuel to Generate Liquid Fuel

Figure 7:
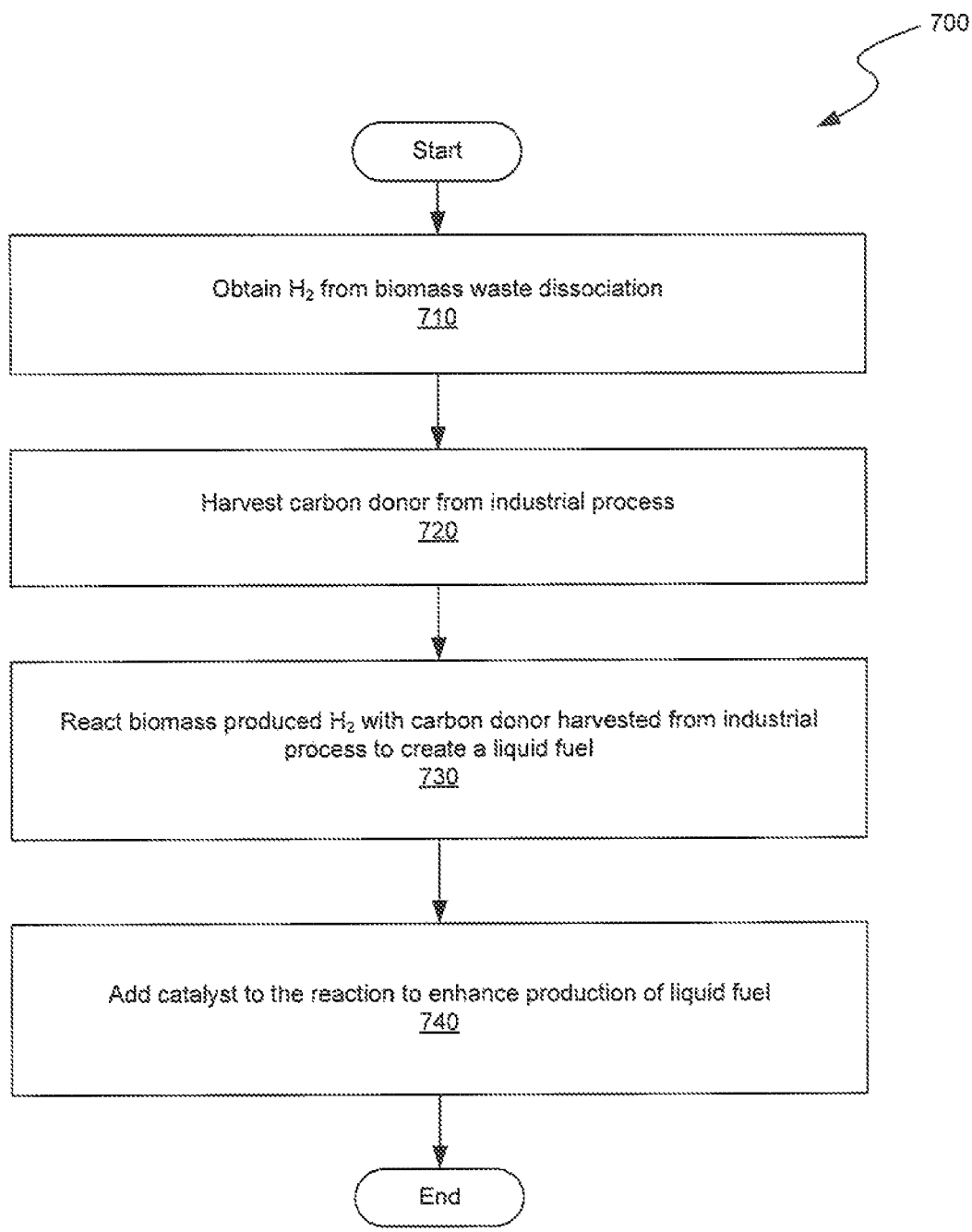
FIG. 7 is a process flow diagram of a process for generating liquid fuel by reinvesting, repurposing, or recycling carbon dioxide harvested from waste generated by industrial processes to react with hydrogen from biomass waste dissociation.

The gaseous fuel can be respeciated to generate liquid fuel, such as alcohols and ammonia as described in U.S. application Ser. No. 13/027,196, filed on Feb. 14, 2011 and incorporated herein by reference in its entirety. For example, FIG. 7 is a process flow diagram of a process 700 for generating liquid fuel by reinvesting, repurposing, or recycling carbon dioxide harvested from waste generated by industrial processes to react with gaseous fuel from biomass waste dissociation. A system (e.g., system 800 below) harvests a carbon donor from industrial processes (720). The carbon donor, such as carbon dioxide or carbon monoxide used in the thermochemical regeneration described herein can be harvested from readily available sources of $CO_2$, such as from central power plants, coking, and calcining operations that burn hydrocarbons, breweries, and bakeries. The system can obtain hydrogen from biomass waste dissociation (710). The harvested $CO_2$ can be used to produce liquid feedstocks for production of chemicals by reacting with the biomass waste produced hydrogen (730). For example, the methanol fuel produced in the described thermochemical regeneration of $CO_2$ with hydrogen can be used to power gasoline and diesel engines adapted to burn such methanol and reduce or eliminate net pollution.

Equations 6 and 7 below illustrate hydrogen and carbon repurposing or recycling via methanol production in which hydrogen (e.g., hydrogen from biomass dissociation) is reacted with carbon monoxide (CO) and $CO_2$ (e.g., from industrial processes), respectively.

$$CO+2H_2 \rightarrow CH_3OH (\Delta H=-21.66 \text{ Kcal/g-mol}) \quad \text{Equation 6}$$

$$CO_2+3H_2 \rightarrow CH_3OH+H_2O (\Delta H=-11.83 \text{ kcal/g-mol}) \quad \text{Equation 7}$$

The described thermochemical regeneration reactions that recycle, or repurpose hydrogen, CO, and $CO_2$ provide a bridge technology for increasing the financial return on past investments in equipment. For example, existing transportation engines and storage tanks can be used to perform thermochemical regeneration reactions to produce fuels that promote longer engine life and greater fuel efficiency along with greatly reduced emissions of carbon dioxide, oxides of nitrogen, and particulates.

The methanol synthesis process summarized in Equations 6 and 7 can be implemented by various steps including ion-induced or catalytic synthesis at 95 to 100 atmospheres pressure and 500° F. (260° C.) (740). Catalysts for the processes of Equations 6 and 7 can include copper-zinc-oxide and deposited sinter mixtures of copper and copper-zinc oxide at various process synthesis conditions including about 260° C. (500° F.) and 1500 psi to produce methanol or methanol and water as shown. Alternatively, dimethyl ether (DME) ethylene, diethyl ether (DEE), or propylene can be produced depending on the pressure, temperature, and catalysts chosen.

Methanol produced by the thermochemical regeneration reactions as described above (see Equations 6 and 7) can be inexpensive, storable, and transportable, in one implementation of the present technology, methanol is synthesized from sources that ordinarily source emissions of $CO_2$. Such $CO_2$ can be captured from ethanol plants, bakeries, breweries, Portland cement plants, and fossil burning power plants and/or by atmospheric "scrubbing" to extract up to about three molecules of carbon dioxide from ten thousand molecules of air.

Similar to ethanol, methanol can be blended with gasoline up to 20% in conventional engines and 85% in flex fuel vehicles with no modifications to the vehicle or existing transportation fuel infrastructure. For years, methanol with an octane rating of 100 has been used as a racing fuel for high-performance cars and dragsters.

Primary use of alcohols, such as methanol, as energy carriers is economically and energetically favorable. For example, one liter of methanol at ambient temperature contains more hydrogen than one liter of liquid hydrogen that must be maintained in storage at −252° C.

Figure 8:
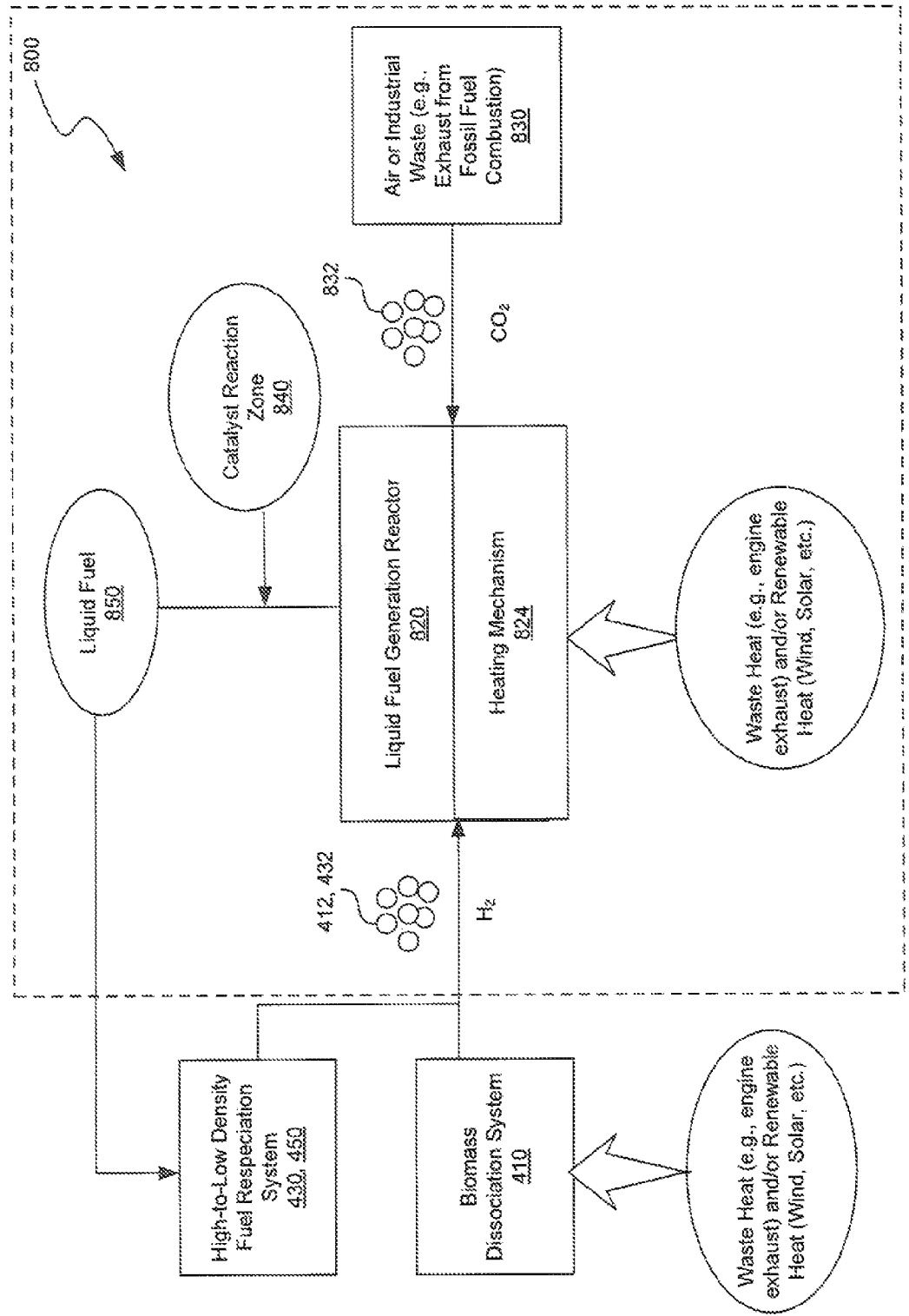
FIG. 8 is a block diagram showing an exemplary system for repurposing or recycling $CO_2$ harvested from industrial processes as waste to create renewable fuel by reacting with biomass produced hydrogen.

FIG. 8 is a block diagram showing an exemplary system 800 for repurposing or recycling $CO_2$ harvested from industrial processes as waste to create renewable fuel by reacting with a hydrogen donor such as biomass produced hydrogen. The system 800 receives the gaseous fuel 412, 432 from the biomass digestion or dissociation system 410 or the high-to-low density fuel respeciation system 430, 450. The heat used to enable digestion and/or more directly dissociate the biomass waste can include waste heat from engine exhausts, engine cooling systems, etc. that otherwise would be released to the environment. Also, one or more renewable energy sources, such as wind, solar, etc., can be used to generate the heat.

The received gaseous fuel (from dissociation of hydrocarbons, for example) is captured and forwarded to liquid fuel generating reactor 820, which includes a heating mechanism 824. The liquid fuel generating reactor 820 also receives carbon donors, such as $CO_2$ 832 harvested from air or industrial processes 830 (e.g., exhaust gases from digestion, fermentation, or from fossil fuel combustion). The liquid fuel generating reactor 820 causes the hydrogen to react with the harvested carbon donors, such as $CO_2$ 832, to generate liquid fuel 850, such as methanol. The carbon donor 832 can be obtained from air or industrial waste 830, including stack smoke, a waste stream of a polymer plant, etc.

The system 800 can include a catalyst reaction zone 840 to receive one or more catalysts that enhance the generation of the liquid fuel. Examples of catalysts are described above.

The generated fuel 850 is storable and transportable. The liquid fuel 850 operates as a vehicle for carrying energy to a desired destination. The liquid fuel 850 can be self-transported to a high-to-low density fuel respeciation system (e.g., 430 or 450).

In some implementations, pressurized hydrogen or pressurized and heated hydrogen can be added to pressurize the products of reacting hydrogen and CO to form a desired compound such as DME or methanol as shown in Equation 8.

$$CO+H_2+H_2 \rightarrow CH_3OH \quad \text{Equation 8}$$

Liquid fuel, such as methanol provided by the processes summarized in Equation 8, can readily be stored, transported, metered, and dispensed by equipment and systems typically utilized for diesel gasoline, and, other alcohol fuels.

Repurposing or recycling of oxides of carbon such as carbon dioxide or carbon monoxide from combustion processes generally poses the problem of separation or accommodation of nitrogen contamination. Another process variation for preparation of value from mixtures of reactive ionic species is provided by arc, corona, microwave, or radiative ionization. Mixtures of carbon monoxide, hydrogen, and nitrogen can be reacted to produce $CH_3OH$ and $NH_3$ as shown in Equation 9.

$$CO+5H_2+N_2+ENERGY \rightarrow CH_3OH+2NH_3 \quad \text{Equation 9}$$

Ammonia ($NH_3$) produced by this or other reactions can be safely stored and conveyed. Ammonia provides compact energy storage and can serve as a precursor of hydrogen. Ammonia can be stored in various ways including as a pressurized liquid, a salt (e.g., ammonium chloride), or in activated media such as carbon. Pressurization can be accomplished, for example, by heat addition. Decomposition of ammonia as it passes a catalyst can be utilized to pressurize the $N_2$ and hydrogen products as well as carbon monoxide and hydrogen that can be co-produced from methanol or wet methanol.

Respeciation of Liquid Fuel to Generate Gaseous Fuel

Figure 9:
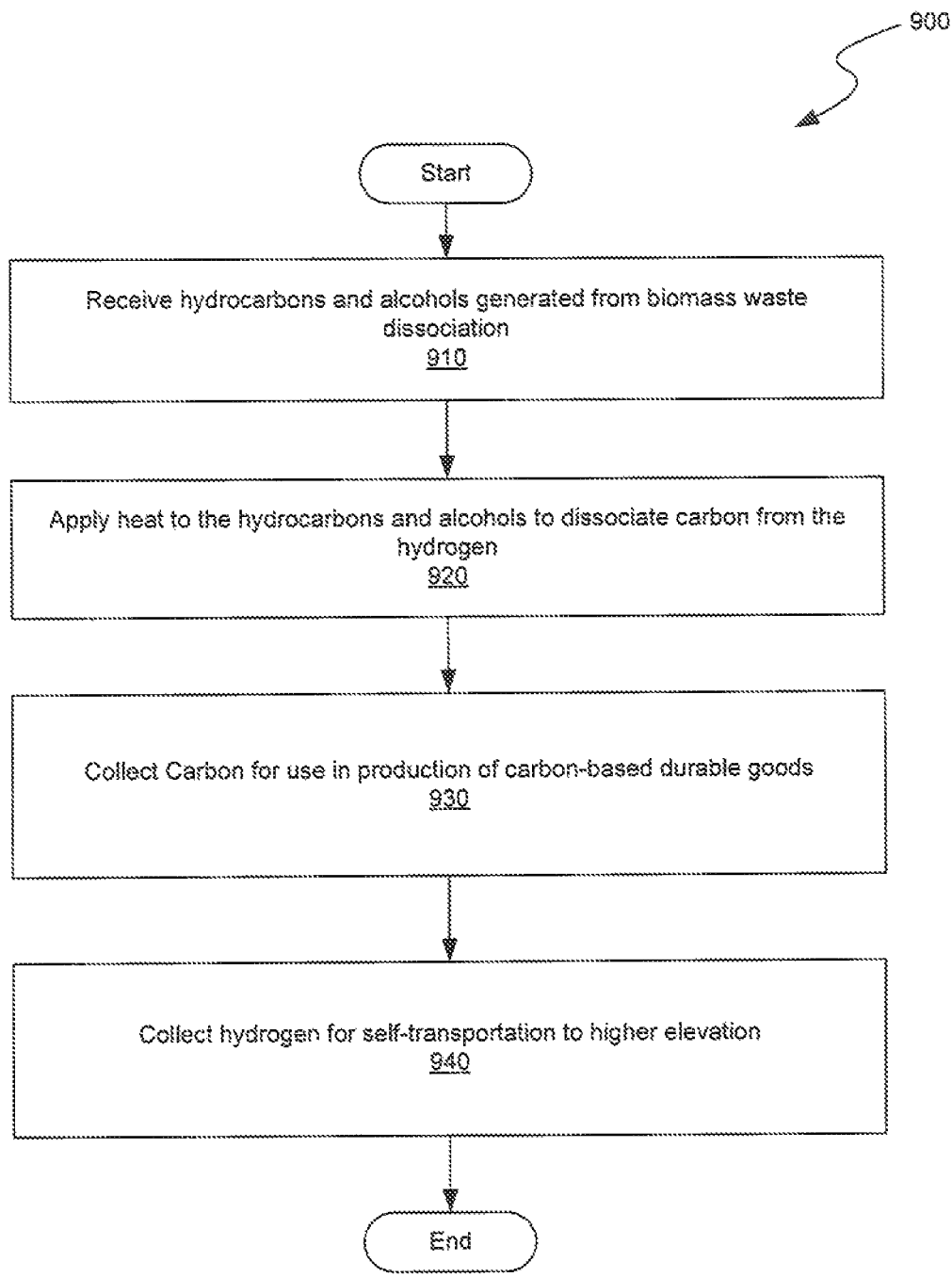
FIG. 9 is a process flow diagram of a process for dissociating hydrocarbons and alcohols to obtain carbon and hydrogen.

The liquid fuel, such as alcohols (e.g., methanol), received from biomass dissociation, the low-to-high density respeciation systems 420 and 440, or another process, can be dissociated to produce gaseous fuel and carbon for a multitude of "specialized carbon" applications ranging from diamond plating and semiconductors to composite structures that are stronger than steel and lighter than aluminum. FIG. 9 is a process flow diagram of a process 900 for dissociating liquid fuels (e.g., alcohols). A reactor (e.g., reactor 1000) can receive liquid fuels (910). The reactor can apply adequate heat and pressure to dissociate carbon from hydrogen (920). Equation 10 shows a reaction for dissociating ethanol by anaerobic decomposition to obtain carbon, carbon monoxide, and hydrogen. A similar reaction can be used to dissociate other fuel alcohols, $$C_2H_5OH + HEAT \rightarrow C + CO + 3H_2 \qquad \text{Equation 10}$$

The carbon monoxide can be reacted in an anaerobic dissociation shown in Equation 11 to increase the yield of hydrogen from feedstocks that contain carbon, hydrogen, and oxygen:

$$CO + H_2O \rightarrow CO_2 + H_2 + HEAT \qquad \text{Equation 11}$$

The total energy value of hydrogen and carbon monoxide produced in the endothermic reactions can be 15 to 20% greater than that of methane used, to source the carbon monoxide and hydrogen as shown in Equation 11. Also, to increase the thermochemical efficiency of the reactions, the heat used to dissociate the liquid fuel can be harvested and recycled from engine exhaust (e.g., waste heat) or a renewable energy source, such as solar or wind energy.

The carbon dissociated in the processes can be collected for use the production of carbon based durable goods (930). For example, the carbon extracted from alcohols can be used to generate carbon products including activated carbon, fibrous carbon, diamond-like coatings, graphitic components, and carbon black. These forms of carbon products can be used to manufacture durable goods, such as better equipment to harness solar, wind, moving water, and geothermal resources along with transportation components that are stronger than steel and lighter than aluminum. Recycling or repurposing carbon to produce equipment that harnesses renewable resources provides many times more energy than burning such carbon one time. Also, gases such as the hydrogen co-produced with carbon from the dissociation of alcohols can be collected for self-transportation to a higher elevation location (940).

FIG. 10 is a block diagram of a system 1000 for respeciating liquid fuel to generate gaseous fuel. In addition, the system 1000 can generate carbon-based durable goods from carbons co-produced with the gaseous fuel. The system 1000 includes a reactor 1010 that receives the liquid fuel, such as alcohols 1016, from the low-to-high density fuel respeciation system 420, 440. The reactor 1010 can include a heating mechanism 1012, such as a heat exchanger for applying the heat used in anaerobic reaction, such as the reaction of Equation 10. The gaseous fuel 1019 generated from dissociation of the liquid fuel, such as alcohols 1016, can be self-transported to a higher elevation location as needed (e.g., to high-to-low density fuel respeciation system 430, 450). Also, the carbon 1017 dissociated from the liquid fuel can be used in production of durable goods 1030.

The reactor 1010 can also include a drying mechanism 1014 for dehydrating alcohols to create DME 1018, which can be used to produce ethylene or propylene 1035. Also, the heating mechanism 1012 can be used in the process to dehydrate the alcohols. The produced ethylene or propylene can be used to generate polymers for producing various plastics and other carbon-based durable goods 1030.

Higher pressure hydrogen can be used to pressurize the products of liquid fuel dissociation, such as carbon monoxide and hydrogen. Also, the higher pressure hydrogen can be produced by other energy induced dissociations including electrolysis of anaerobically developed acids and liquors from organic digestion processes and from water as generally shown in Equations 12 and 13.

$$C_2H_4O_2 + 2H_2O + ENERGY \rightarrow 2CO_2 + 4H_2 \qquad \text{Equation 12}$$

$$H_2O + ENERGY \rightarrow 0.5O_2 + H_2 \qquad \text{Equation 13}$$

Energy and/or Material Transport Process

In several embodiments of a process according to the present technology, gaseous fuel (e.g., gaseous substance such as fuel at controlled temperature and pressure) is provided or generated at a first location. Gaseous substance or fuel such as hydrogen, methane, ethane, butane, propane, carbon monoxide, nitrous oxide, syngas, natural gas, biogas, or another fuel gas alone or in combination with one or more other materials. The gaseous fuel can be provided, for example, by removal from storage or by extraction from a natural source. When the gaseous fuel is provided from a subterranean source, the first location can be a first location below, near, at, or above ground level. Hydrogen in gaseous fuel can be generated, for example, by dissociation, reforming hydrocarbons (e.g., methane) or by electrolysis of water. Hydrogen and/or methane or other suitable compound can be generated from biomass according to one of the processes described above. Raw material for generating the gaseous fuel can be gas (e.g., natural gas), liquid (e.g., liquid biomass), or solid (e.g., solid biomass).

From the first location, gaseous fuel can be transported to a second location having a higher elevation than the first location. For example, gaseous fuel can be transported to the second location through a conduit, such as a pipeline, directly connecting a reactor or storage structure at the first location to a reactor or storage structure at the second location. Transporting gaseous fuel uphill can be more efficient than transporting liquid fuel (e.g., liquid fuel at standard temperature and pressure) uphill. In several embodiments of the present technology, gaseous fuel is provided or generated at pressures greater than atmospheric pressure. Output from a pressurized storage structure or a reactor generating gaseous fuel can be routed directly into the conduit leading to the second location. In this way, pressure from providing or generating the gaseous fuel is harnessed to overcome the pressure drop of the conduit.

If the pressure of the provided or generated gaseous fuel is less than the required pressure to overcome the pressure drop of the conduit or to otherwise increase throughput, one or more boosters can be included before and/or along the conduit. A booster can include a compressor or a source of gaseous fuel at a pressure greater than the pressure of gaseous fuel within the conduit at the position of the booster. An electrolytic booster, for example, can be configured to generate hydrogen from water by electrolysis and to inject the generated hydrogen into the conduit to increase the pressure of gaseous fuel within the conduit. Electrolysis of water also produces oxygen. In several embodiments of the present technology, an electrolytic booster is located near a point-of-use for oxygen, such as a water treatment plant, a hospital, or a smelter. Oxygen from the electrolytic booster can be routed to the point-of-use, for example, through a conduit or by transported containers. Boosters in embodiments of the present technology, such as heaters, mechanical compressors or electrolytic boosters, can be powered by renewable energy, such as solar, wind, or geothermal energy, and can be operated continuously or intermittently according to energy availability. Use of renewable energy is particularly well suited to boosters located along remote portions of large-scale pipelines where other power sources are not available.

At the second location, gaseous substance such as fuel can be processed or reacted to form liquid fuel. Examples of liquid fuel include alcohols (e.g., methanol, ethanol, propanol, and butanol), alkynes (e.g., acetylene), ketones (e.g., acetone), ethers (e.g., dimethyl or diethyl ether), and ammonia. In some embodiments of the present technology, the liquid fuel includes substantially no hydrocarbons or less than about 25% hydrocarbons. Hydrogen can be reacted with nitrogen (e.g., from air) to form ammonia by the Haber process. Alternatively, hydrogen can be reacted with carbon monoxide or carbon dioxide to form methanol according to Equations 6 and 7 above. Methane in the gaseous fuel can be reformed into hydrogen, which can then be reacted to form ammonia or methanol as described above. The conversion of methane into hydrogen can be performed at the first location or the second location. Methane also can be converted directly into methanol without a hydrogen intermediary. Other conversions can be performed according to other processes known in the chemical arts.

Liquid fuel at the second location resulting from reaction of gaseous fuel transported from the first location can be transported to a third location at a lower elevation than the second location. For example, liquid fuel can be transported to the third location through a conduit, such as a pipeline, directly connecting a reactor or storage chamber at the second location to a reactor or storage chamber at the third location. The elevation of the third location can be higher or lower than the elevation of the first location. A portion of the potential energy difference between liquid fuel at the second location and liquid fuel at the third location can be captured to perform useful work. For example, liquid fuel can turn a turbine as it moves from the second location to the third location. Liquid fuel also can reach the third location under pressure. In several embodiments of the present technology, the third location is one of many locations to which the liquid fuel is distributed. As described below, these locations can be point-of-partial delivery or point-of-use locations.

If the liquid fuel is plot used at the third location, the cycle can continue by converting the liquid fuel into gaseous fuel to be transported to a fourth location at a higher elevation than the third location. For example, ammonia can be converted into hydrogen by catalytic or thermal dissociation or electrolysis. Methanol can be reacted with water to form hydrogen by catalytic or thermal dissociation or electrolysis or reacted with an oxidant or water to form hydrogen according to Equations 12 and 13 above. At the fourth location, the gaseous fuel can be used (e.g., distributed to multiple point-of-use locations) or converted into liquid fuel and transported to a fifth location at a lower elevation than the fourth location. At the fifth location, the liquid fuel can be used or further converted and transported. Embodiments of the present technology can include an unlimited number of additional steps in which gaseous fuel is converted into liquid fuel and transported to a lower elevation or liquid fuel is converted into gaseous fuel and transported to a higher elevation. Intervening transporting steps using conventional transporting processes (e.g., tankers) also can be included. As with the boosters described above, the reactors to convert gaseous fuel into liquid fuel or liquid fuel into gaseous fuel can be powered by renewable energy, such as solar, wind, or geothermal energy, and can be operated continuously or intermittently according to energy availability.

The locations described in embodiments of the present technology can be separated by various distances. On a small scale, successive locations can be a few hundred meters from each other and can utilize insulated piping to deliver substances that are gaseous or vaporous if kept warmer than the environment or to similarly deliver liquids that are kept cooler than the environment. On a larger scale, the distances between successive locations can be much greater, such as between about 1 km and about 100 km. As discussed above, small scale embodiments can be used, for example, in urban areas having manmade elevation changes. Large scale embodiments can be used, for example, to transport fuel across significant expanses of terrain having natural elevation changes. With exception, when the distances between successive locations are greater, the elevation differences between successive locations are also greater. The elevation differences can be, for example, between about 10 m and about 5 km, such as between about 100 m and about 4 km, or between about 200 m and about 3 km. Embodiments of the present technology that include multiple cycles and, in some cases, intervening transporting steps, can provide energy transport on a transcontinental or transoceanic scale. The first location and the last location in several embodiments of a process according to the present technology are between about 100 m and about 5,000 km from each other, such as between about 1 km and about 1,000 km or between about 5 km and about 500 km from each other.

In addition to being used or further transported at or between each location, gaseous fuel and liquid fuel can be stored at or between each location. For example, liquid fuel can be stored at a higher elevation location prior to being transported to a lower elevation location. Similar to water in a water tower, liquid fuel stored at a higher elevation location can be distributed to point-of-use locations (e.g., ammonia to fertilizer production plants and methanol to vehicle fueling stations) at lower elevations with gravity providing the necessary pressure. A portion of the potential energy of liquid fuel stored at the higher elevation location also can be captured to perform other useful work, such as turning a turbine. Liquid fuel also can be stored at a lower elevation location, converted into gaseous fuel and then transported to a higher elevation location. Gaseous fuel typically is less efficient to store than liquid fuel because it typically must be pressurized. Embodiments of processes and systems according to the present technology, however, can include storage of gaseous fuel at or between locations. For example, gaseous fuel can be stored at a lower elevation location prior to being transported to a higher elevation location. Gaseous fuel also can be stored at a higher elevation location, converted into liquid fuel, and then transported to a lower elevation location. When stored under pressure, gaseous fuel can form a liquid phase.

Gaseous fuel and liquid fuel in embodiments of the present technology can be stored, for example, in natural or manmade structures. Such structures can be above or below ground. Gaseous fuel and liquid fuel in embodiments of the present technology also can be stored in conduits (e.g., pipelines). For example, gaseous fuel can be stored in a conduit configured to transport gaseous fuel from a lower elevation location to a higher elevation location and liquid fuel can be stored in a conduit configured to transport liquid fuel from a higher elevation location to a lower elevation location. Materials for vessels, pipelines, and other structures of systems according to embodiments of the present technology can be selected, to prevent corrosion. For example, vessels and pipelines intended to store ammonia and other materials that are highly corrosive to metal can include a corrosion-resistant lining such as a fluoropolymer or other polymer lining.

In several embodiments of the present technology, gaseous fuel or liquid fuel is stored underground, such as in underground vessels or in natural structures (e.g., geological formations). Natural structures include depleted natural gas reservoirs, aquifers, and salt caverns. Gaseous fuel typically is better suited than liquid fuel for storage in natural structures because liquid fuel can be difficult to remove. In contrast, gaseous fuel typically can be pumped into natural structures until it reaches high pressures that facilitate its eventual removal. As described above, pressure from providing or generating gaseous fuel can be used to transport the gaseous fuel from a lower elevation location to a higher elevation location. This can occur at the origination of the process (e.g., at an initial reactor or source) or at any subsequent location preceding a higher elevation location.

In addition to transporting energy, embodiments of the present technology can be used to transport material without transporting energy or substances may be mixed or travel in parallel including the use of coaxial conduits in which one fluid insulates the other to synergistically deliver both energy and non-energy substances. Such embodiments are described, for example, by substituting "gaseous material" for "gaseous fuel" as used elsewhere in this disclosure and substituting "liquid material" for "liquid fuel" as used elsewhere in this disclosure except where the context refers to specific fuel types. In one example of a material transport process according to the present technology, the gaseous material is sulfur dioxide and the liquid material is sulfuric acid. Sulfur dioxide can be converted into sulfuric acid, for example, by the contact process, the wet sulfuric acid process, or another process known in the chemical arts. In another example, the gaseous material is chlorine and the liquid material is hydrochloric acid. Chlorine can be reacted with hydrogen, for example, to form hydrochloric acid.

Energy and/or Material Transport System

Figure 11:
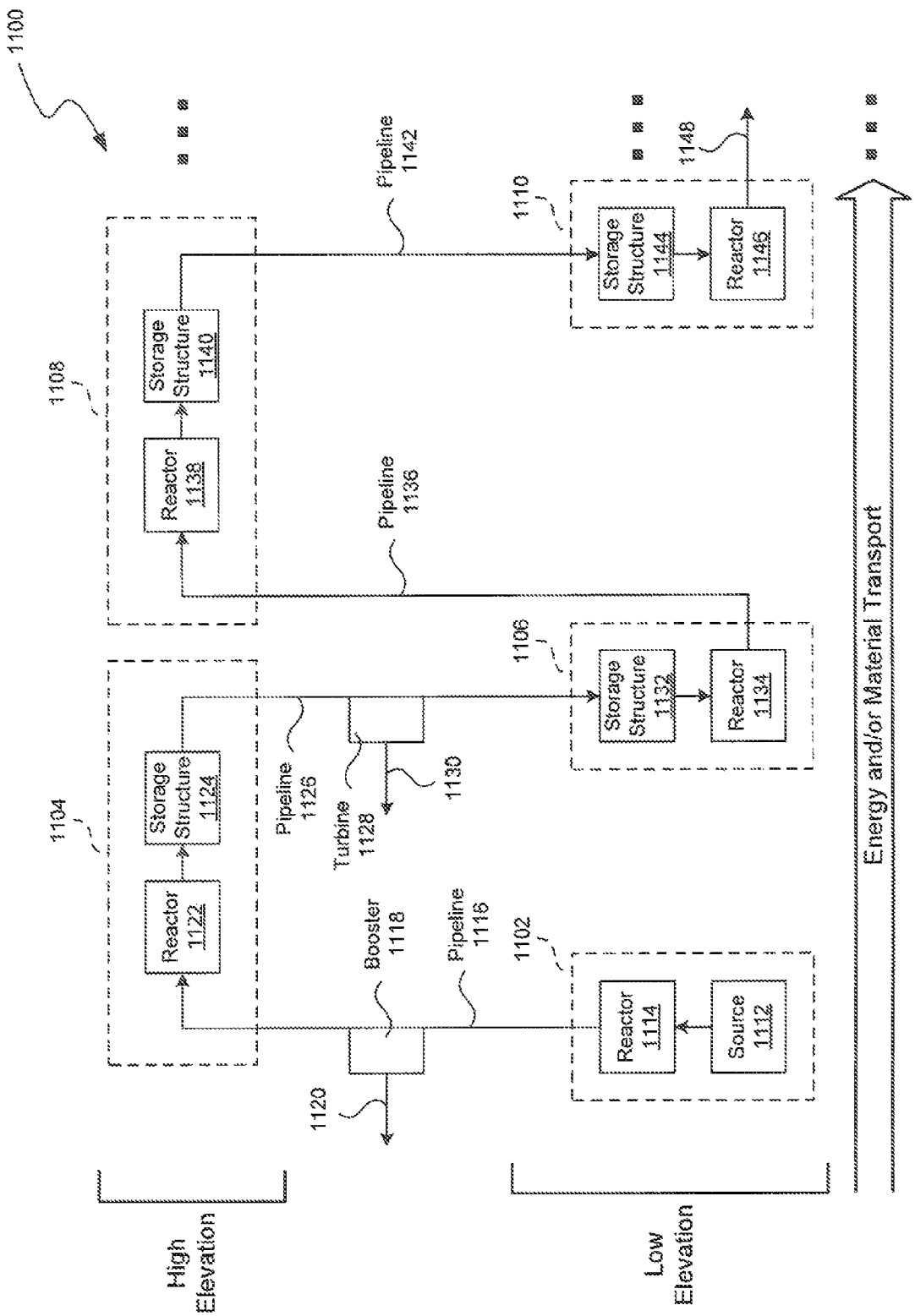
FIG. 11 is block diagram of a system according to another embodiment of the present technology.

FIG. 11 illustrates a system 1100 configured for energy and/or material transport according to an embodiment of the present technology. The system 1100 shown in FIG. 11 is described below relative to its features and the features of exemplary processes for which the system and portions of the system can be configured. As shown in FIG. 11, the system 1100 includes a first location 1102, a second location 1104, a third location 1106, a fourth location 1108, and a fifth location 1110. The first, third and fifth locations 1102, 1106, 1110 are located at a lower elevation. The second and fourth locations 1104, 1108 are located at a higher elevation. The elevation differences are represented schematically only and need not be similar between the first, third and fifth locations 1102, 1106, 1110 and between the second and fourth locations 1104, 1108. Aside from the elevation relationships between adjacent locations, the elevation relationships between a location and non-adjacent locations do not necessarily to low a predetermined pattern. For example, the fifth location 1110 can be higher or lower than the first, second, and third locations 1102, 1104, 1106. Furthermore, embodiments of the disclosed system can include intervening locations within a pattern of adjacent locations.

The first location 1102 includes a source 1112 and a reactor 1114. Raw material from the source 1112 enters the reactor 1114 where it is converted into gaseous fuel. Gaseous fuel exiting the reactor 1114 is transported through a pipeline 1116 including a booster 1118. The booster 1118 is an electrolytic booster that generates hydrogen and oxygen by electrolysis of water. The booster 1118 can include a power generator (not shown) configured to generate power from a renewable source. Hydrogen from the booster 1118 enters the pipeline 1116 to supplement the pressure of the gaseous fuel Oxygen from the booster 1118 travels to a point-of-use (not shown) through a conduit 1120. From the portion of the pipeline including the booster 1118, gaseous fuel travels to a reactor 1122 at the second location 1104. Energy from pressure and/or glow of the gaseous fuel is converted into electrical energy at the turbine 1127, which is then routed to a point-of-use (not shown). Within the reactor 1122, gaseous fuel is converted into liquid fuel, which is then routed into a storage structure 1124. From the storage structure 1124, liquid fuel travels through a pipeline 1126 including a turbine 1128. Energy from flow of the liquid fuel is converted into electrical energy at the turbine 1128, which is then routed to a point-of-use (not shown) through an electrical cable 1130. Liquid fuel then travels to a storage structure 1132 at the third location 1106. Liquid fuel from the storage structure 1132 is fed into a reactor 1134 in which it is converted into gaseous fuel, which is then routed through a pipeline 1136 to a reactor 1138 at the fourth location 1108. Energy from pressure and/or flow of the gaseous fuel is converted into electrical energy at the turbine 1137, which is then routed to a point-of-use (not shown). Within the reactor 1138, gaseous fuel is converted into liquid fuel, which moves from the reactor 1138 into a storage structure 1140. From the storage structure 1140, the liquid fuel travels through a pipeline 1142 to a storage structure 1144 at the fifth location 1110. Liquid fuel from the storage structure 1144 is fed into a reactor 1146 in which it is converted into gaseous fuel, which is then routed through a pipeline 1148 for further transport (not shown).

Figure 12:
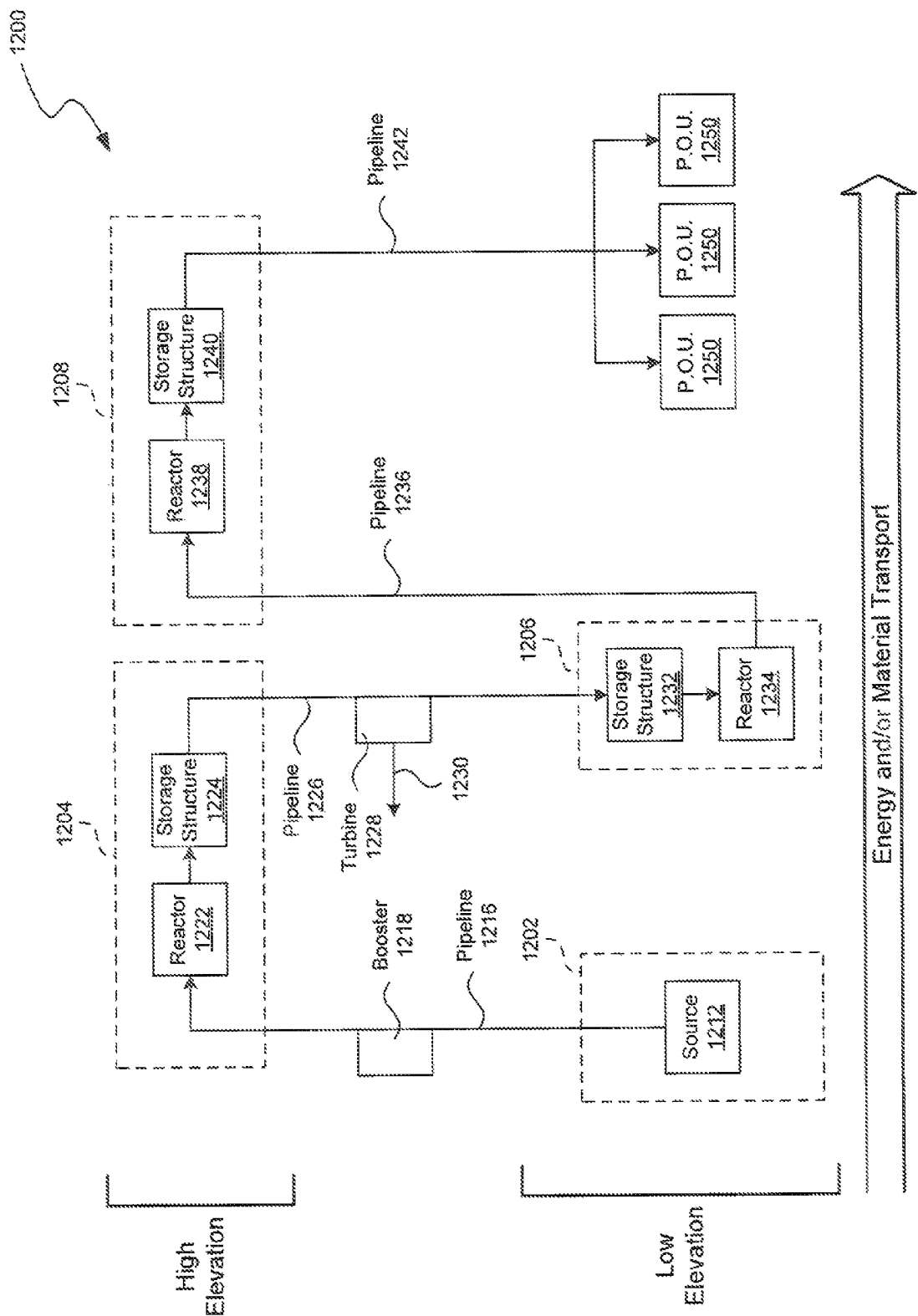
FIG. 12 is block diagram of a system according to another embodiment of the present technology.

FIG. 12 illustrates a system 1200 configured for fuel transport and storage according to another embodiment of the present technology. The system 1200 shown in FIG. 12 is described below relative to its features and the features of exemplary processes for which the system and portions of the system can be configured. The first two digits of the reference numbers shown in FIG. 12 are "12." The final two digits of the reference numbers shown in FIG. 12 are identical to the final two digits of the reference numbers shown in FIG. 11 for similar or identical elements. Unlike the system 1100 shown in FIG. 11 the system 1200 shown in FIG. 12 does not include a reactor at the first location 1202. Instead, the pipeline 1216 extends directly from the source 1212 at the first location 1202 to the reactor 1222 at the second location 1204. This configuration is particularly well suited to implementations in which gaseous fuel from the source 1212 is collected under pressure, such as from a pressurized storage structure. Also unlike the system 1100 shown in FIG. 11, the system 1200 shown in FIG. 12 includes a booster 1218 without a conduit for delivering oxygen to a point-of-use. Rather than an electrolytic booster, the booster 1218 shown in FIG. 12 is a simple heater and/or simple compressor. A simple heater and/or compressor can be preferable to an electrolytic booster, for example, when the gaseous fuel in the pipeline 1216 includes little or no hydrogen.

Instead of the fifth location 1110 of the system 1100 shown in FIG. 11, the system 1200 shown in FIG. 12 includes three point-of-use locations 1250 after the pipeline 1242. The point-of-use locations 1250 are represented schematically only. The point-of-use locations 1250 need not have similar elevations and can be located after branches of the pipeline 1242 of varying lengths. Other embodiments of a system according to the present technology can include a different number of point-of use locations, such as one, two, or a greater number of point-of-use locations.

Systems according to embodiments of the present technology can have many variations relative to the systems 1100, 1200 shown in FIGS. 11 and 12. The systems can be configured for continuous and/or batch operation. Storage structures can be deleted or added at any point before, after, or along the pipelines. For example, the system 1100 shown in FIG. 11 can include storage structures after the reactors 1114, 1134, 1146 and/or before the reactors 1122, 1138. The pipelines 1116, 1136, 1216, 1236 can include no boosters, one booster, two boosters, or a greater number of boosters at various positions. Similarly, the pipelines 1126, 1142, 1226, 1242 can include no turbines, one turbine, two turbines or a greater number of turbines at various positions. The net elevation changes of the pipelines 1116, 1126, 1136, 1142, 1216, 1226, 1236, 1242 are represented schematically in FIGS. 11 and 12, but the pipelines can have varying elevation changes along their length, such as to accommodate environmental topography.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should, not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

U.S. application Ser. No. 13/027,197, filed Feb. 14, 2011 and incorporated herein by reference in its entirety includes additional disclosure concerning isolating contaminants in liquid fuels. Such liquid fuels can be used in several embodiments of the present technology. Furthermore, processes, devices, and materials disclosed in referenced U.S. application Ser. Nos. 13/027,068, 13/027,196 and 13/027,197 can be useful in implementing several embodiments of the present technology. To the extent the disclosure in the referenced applications conflicts with other disclosure presented herein, the disclosure presented herein controls.

I claim:

1. A method for transporting energy and/or material, comprising:
providing or forming a first gaseous material at a first location;
transporting by expansion the first gaseous material from the first location to a second location having a higher elevation than the first location;
reacting the first gaseous material to form a first liquid material at the second location;
transporting by gravitational acceleration the first liquid material from the second location to a third location having a lower elevation than the second location;
reacting the first liquid material to form a second gaseous material at the third location;
transporting the second gaseous material to a fourth location having a higher elevation than the third location;
reacting the second gaseous material to form a second liquid material at the fourth location; and
transporting the second liquid material to a fifth location having a lower elevation than the fourth location.

2. The method of claim 1, wherein reacting the first liquid material includes reacting the first liquid material anaerobically.

3. The method of claim 1, wherein a pressure from providing or forming the first gaseous material accounts for all or a portion of an energy used to transport the first gaseous material from the first location to the second location.

4. The method of claim 1, wherein a pressure from forming the second gaseous material accounts for all or a portion of an energy used to transport the second gaseous material from the third location to the fourth location.

5. The method of claim 1, further comprising extracting energy with a turbine from flow of the first liquid material from the second location to the third location.

6. The method of claim 1, further comprising extracting energy with a turbine from flow of the second liquid material from the fourth location to the fifth location.

7. The method of claim 1, wherein transporting the second liquid material from the fourth location to the fifth location includes gravity transporting the second liquid material.

8. The method of claim 1, wherein the first gaseous material and the second gaseous material include hydrogen, methane, ethane, butane, propane, carbon monoxide, nitrous oxide, or a combination thereof.

9. The method of claim 1, wherein the first liquid material and the second liquid material include an alcohol, an alkyne, a ketone, an ether, ammonia, or a combination thereof.

10. The method of claim 1, wherein the first gaseous material and the second gaseous material include hydrogen, methane, or a combination thereof, and the first liquid material and the second liquid material include methanol, ammonia, or a combination thereof.

11. The method of claim 1, wherein the first gaseous material and the second gaseous material include sulfur dioxide, chlorine, or a combination thereof, and the first liquid material and the second liquid material include sulfuric acid, hydrochloric acid, or a combination thereof.

12. The method of claim 1, wherein a distance between the first location and the fifth location is between about 1 km and about 1,000 km.

13. The method of claim 1, wherein an elevation difference between the first location and the second location and an elevation difference between the third location and the fourth location are between about 100 m and about 4 km.

14. The method of claim 1, further comprising generating a supplemental gaseous material and injecting the supplemental gaseous material into the first gaseous material to increase a pressure of the first gaseous material as it travels from the first location to the second location or injecting the supplemental gaseous material into the second gaseous material to increase a pressure of the second gaseous material as it travels from the third location to the fourth location.

15. The method of claim 14, wherein the supplemental gaseous material includes hydrogen, and the method further comprises generating oxygen in conjunction with generating the supplemental gaseous material, and delivering the oxygen to a point-of-use location.

16. The method of claim 1, wherein the first gaseous material, the second gaseous material, the first liquid material, and the second liquid material are a first gaseous fuel, a second gaseous fuel, a first liquid fuel, and a second liquid fuel, respectively.

17. The method of claim 16, wherein the first liquid fuel includes less than about 25% hydrocarbons.

18. The method of claim 1, wherein the fifth location is a point-of-use location and gravity provides all or a portion of a pressure head of the second liquid material at the point-of-use location.

19. The method of claim 18, wherein the point-of-use location is a first point-of-use location, and the method further comprises transporting the second liquid material from the fourth location to a second point-of-use location having a lower elevation than the fourth location, wherein gravity provides all or a portion of a pressure head of the second liquid material at the second point-of-use location.

20. A method for transporting energy and/or material, comprising:
providing or forming a first gaseous fuel at a first location and a first elevation;
transporting the first gaseous fuel from the first location to a second location having a second elevation;
reacting the first gaseous fuel to form a first liquid fuel at the second location;
transporting the first liquid fuel from the second location to a third location having a third elevation;
extracting energy with a turbine from flow of the first liquid fuel from the second location to the third location;
reacting the first liquid fuel to form a second gaseous fuel at the third location;
transporting the second gaseous fuel to a fourth location having a fourth elevation;
reacting the second gaseous fuel to form a second liquid fuel at the fourth location;
transporting the second liquid fuel to a fifth location having a fifth elevation; and
extracting energy with the turbine from flow of the second liquid fuel from the fourth location to the fifth location, wherein a pressure from providing or forming the first gaseous fuel accounts for all or a portion of an energy used to transport the first gaseous fuel from the first location to the second location, and a pressure from forming the second gaseous fuel accounts for all or a portion of an energy used to transport the second gaseous fuel from the third location to the fourth location.

21. The method of claim 15, wherein generating the supplemental gaseous material includes generating the supplemental gaseous material by electrolysis of water.

22. The method of claim 1, wherein:
the first gaseous material is carbon dioxide or carbon monoxide; and
the first liquid material is an alcohol.

23. The method of claim 1, wherein:
the first location is a base of a building; and
the second location is a top of a building.

24. The method of claim 1, wherein an elevation difference between the first and second locations is due to natural topography.

25. The method of claim 1, wherein transporting the first gaseous material includes transporting the first gaseous material through a pipeline directly connecting a first reactor or storage chamber at the first location to a second reactor or storage chamber at the second location.

26. The method of claim 1, further comprising dissolving a hazardous contaminant into the first liquid material.

27. The method of claim 26, wherein the first liquid material is a fuel.

28. The method of claim 1, wherein:
the first gaseous material is hydrogen;
the first liquid material is ammonia; and
reacting the first gaseous material to form the first liquid material includes reacting the hydrogen with nitrogen from air at the second location.

29. The method of claim 28, wherein providing or forming the first gaseous material includes reforming methane from biomass dissociation at the first location.

* * * * *